US010865392B2

(12) United States Patent
Farrell et al.

(10) Patent No.: US 10,865,392 B2
(45) Date of Patent: Dec. 15, 2020

(54) ACETYL TRANSFERASES AND THEIR USE FOR PRODUCING CAROTENOIDS

(71) Applicant: DSM IP Assets B.V., Heerlen (NL)

(72) Inventors: Christopher Farrell, Lexington, MA (US); Peter Houston, Lexington, MA (US); Lisa Laprade, Lexington, MA (US); Nathalie Balch, Tewksbury, MA (US); Maria Mayorga, Medford, MA (US)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/593,509

(22) Filed: Oct. 4, 2019

(65) Prior Publication Data

US 2020/0123507 A1  Apr. 23, 2020

Related U.S. Application Data

(62) Division of application No. 14/650,298, filed as application No. PCT/IB2013/058049 on Aug. 28, 2013, now Pat. No. 10,465,174.

(60) Provisional application No. 61/830,234, filed on Jun. 3, 2013.

(30) Foreign Application Priority Data

Dec. 20, 2012 (EP) .................................. 12198373

(51) Int. Cl.
C12N 9/10 (2006.01)
C12P 23/00 (2006.01)
(52) U.S. Cl.
CPC ............ *C12N 9/1029* (2013.01); *C12P 23/00* (2013.01); *C12Y 203/01084* (2013.01)
(58) Field of Classification Search
CPC .................................................. C12N 9/1029
USPC ......................................................... 435/15
See application file for complete search history.

(56) References Cited

U.S. PATENT DOCUMENTS

| 7,851,199 | B2 | 12/2010 | Bailey et al. | |
| 10,465,174 | B2 * | 11/2019 | Farrell | C12N 9/1029 |
| 2010/0180491 | A1 | 7/2010 | Lee et al. | |
| 2010/0297722 | A1 | 11/2010 | Anterola et al. | |
| 2015/0322412 | A1 | 11/2015 | Farrell et al. | |

FOREIGN PATENT DOCUMENTS

| EP | 0574941 A2 | 12/1993 |
| WO | WO-2002099095 A2 | 12/2002 |
| WO | WO-2009037329 A2 | 3/2009 |

OTHER PUBLICATIONS

Abelson et al., "Guide to Yeast Genetics and Molecular Biology," Methods in Enzymology, (BOOK) (1994).
Amberg et al., "Methods in Yeast Genetics," Cold Spring Harbor Laboratory Course Manual (BOOK) (2005).
Ausubel et al., "Current Protocols in Molecular Biology," (BOOK), Wiley Interscience, New York (1997).
Bolker et al., "Tagging Pathogenicity Genes in *Ustilago maydis* by Restriction Enzyme-Mediated Integration (REMI)," Mol Gen Genet, 248:547-552, (1995).
Borneman, et al., "Whole-Genome Comparison Reveals Novel Genetic Elements that Characterize the Genome of Industrial Strains of *Saccharomyces cerevisiae*," Novel Genetic Elements in Industrial Yeasts, PLoS Genetics, www.plosgenetics.org, vol. 7, Issue 2, e1001287, Feb. 2011.
Borneman et al., XP-002717048, "Whole-genome comparison reveals novel genetic elements that characterize the genome of industrial strains of *Sacchromyces cerevisiae*," PLoS Genet. 7:E1001287-E1001287, www.uniprot.org/uniprot/E7KIN6.txt, Apr. 5, 2011.
Borneman et al., XP-002719365, "Whole-genome comparison reveals novel genetic elements that characterize the genome of industrial strains of *Sacchromyces cerevisiae*," PLoS Genet. 7:E1001287-E1001287, www.uniprot.org/uniprot/E7QL60.txt, Apr. 5, 2011.
Brown et al., "Stable Transformation and Regulated Expression of an Inducible Reporter Construct in *Candida albicans* using Restriction Enzyme-Mediated Integration," Mol Gen. Genet, 251:75-80, (1996).
Cliften et al; XP-002719366, "Finding functional features in *Saccharomyces* genomes by phylogenetic footprinting," Science 301:71-76, www.uniprot.org/uniprot/J4U1K1.txt, Oct. 31, 2012.
Fujii et al., "Molecular Cloning, Sequence Analysis, and Expression of the Yeast Alcohol Acetyltransferase Gene," Applied and Environmental Microbiology, 60(8), 2786-2792, (1994).
Fujii et al., "Nucleotide Sequences of Alcohol Acetyltransferase Genes from Lager Brewing Yeast," Yeast, 12:593-598, (1996).
Glover et al., "DNA Cloning," vol. 1, (BOOK), 1, IRL Press (1995).
Guo et al; "Protein Tolerance to Random Amino Acid Change," Proc. Natl. Acad. Sci. U.S.A. 101(25):9205-9210. Epud. Jun. 22, 2004.
Ishchuk et al., Heterologous Expression of *Saccharomyces cerevisiae* MPR1 Gene Confers Tolerance to Ethanol and L-Azetidine-2-Carboxylic Acid in *Hansenula polymorpha*, J. Ind. Microbiol Biotechnol 37:213-218 (2010).
Sambrook, J., "Molcular Cloning," A Laboratory Manual, Table of contents, Second (1989).
Liti et al; XP-002719367, "High Quality De Novo Sequencing and Assembly of the *Saccharomyces arboricolus* Genome," www.uniprot.org/uniprot/J8Q1N7.txt, Oct. 31, 2012.
Lu et al., "Carotenoid Metabolism: Biosynthesis, Regulation, and Beyond," J. Integr. Plant Biol. 50(7):778-785, Jul. 2008.
Needleman et al., "A General Method Applicable to the Search for Similarities in the Amino Acid Sequence of Two Proteins," J. Mol. Biol., 48:443-453, (1970).

(Continued)

*Primary Examiner* — Sheridan Swope
(74) *Attorney, Agent, or Firm* — Nixon & Vanderhye, PC

(57) ABSTRACT

The present invention relates to acetyl transferases, nucleic acid sequences coding therefore, expression constructs and vectors comprising these sequences, microorganisms transformed therewith and use thereof.

6 Claims, 4 Drawing Sheets

Specification includes a Sequence Listing.

(56) References Cited

OTHER PUBLICATIONS

Nisar et al., "Carotenoid Metabolism in Plants," Molecular Plant vol. 8, Issue 1, pp. 68-82, Jan. 5, 2015.
"Nomenclature Committee of the International Union of Biochemistry and Molecular Biology (NC-IUBMB) Enzyme Classification," Acetyl transferase E.C. numbers. Downloaded Jul. 17, 2018.
Pouwels et al., "Elsevier," (BOOK), Amsterdam-New York, Oxford (1985).
Rice et al., "EMBOSS: The European Molecular Biology Open Software Suite," Resource Internet, 16(6):276-277, (2000).
Schiestl et al., "Integration of DNA Fragments by Illegitimate Recombination in *Saccharomyces cerevisiae*," Proc. Natl. Acad. Sci., 88:7585-7589, (1991).
Yow et al; Physiological Role of D-Amino Acid-N-Acetyltransferase of *Saccharomyces cerevisiae*: Detoxification of D-Amino Acids, Arch. Microbiol 185:39-46 (2006).

* cited by examiner

Fig. 3 (Zxt)
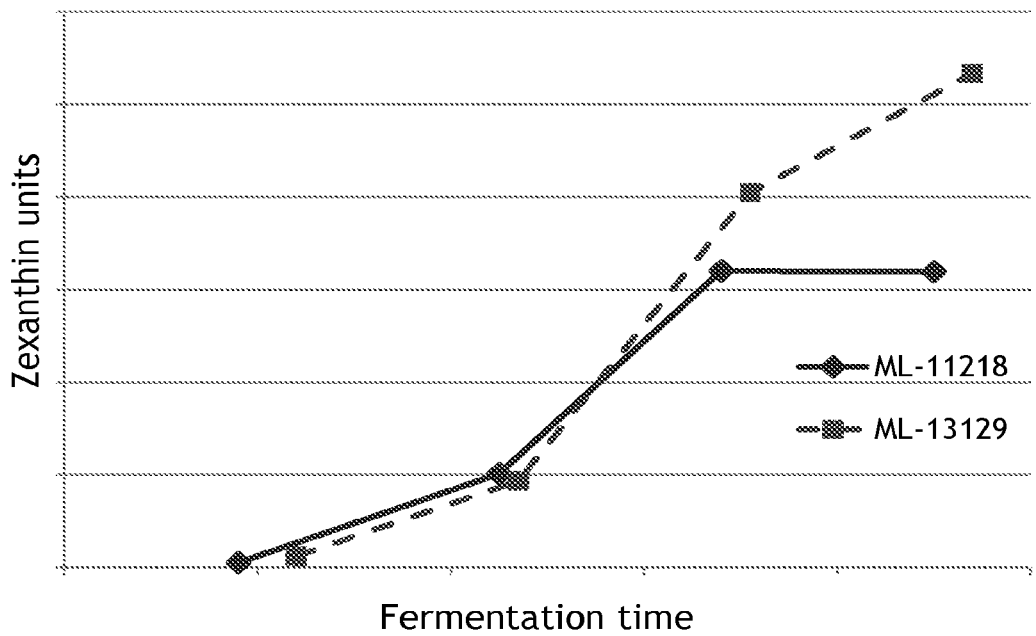
Fig 4 (Axt)
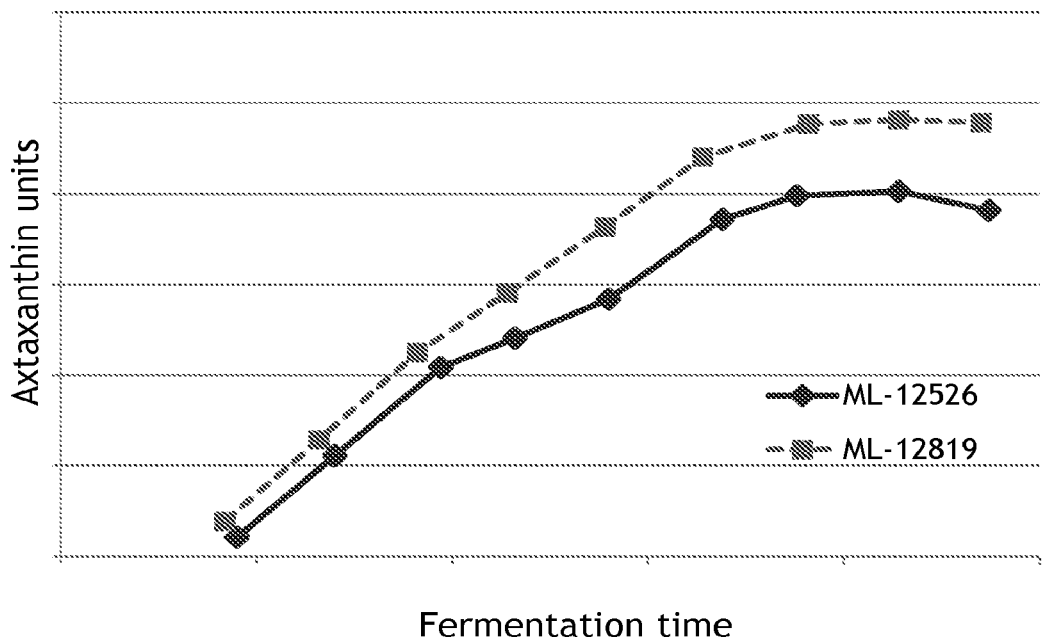

Fig. 6 (Zxt)
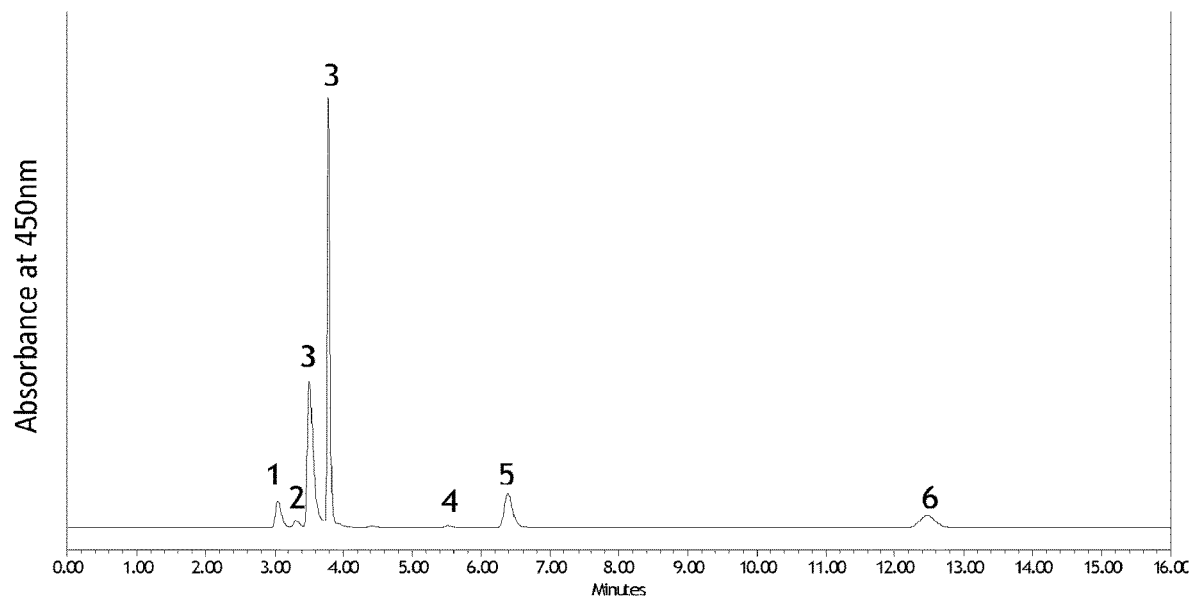
Fig. 7 (Axt)
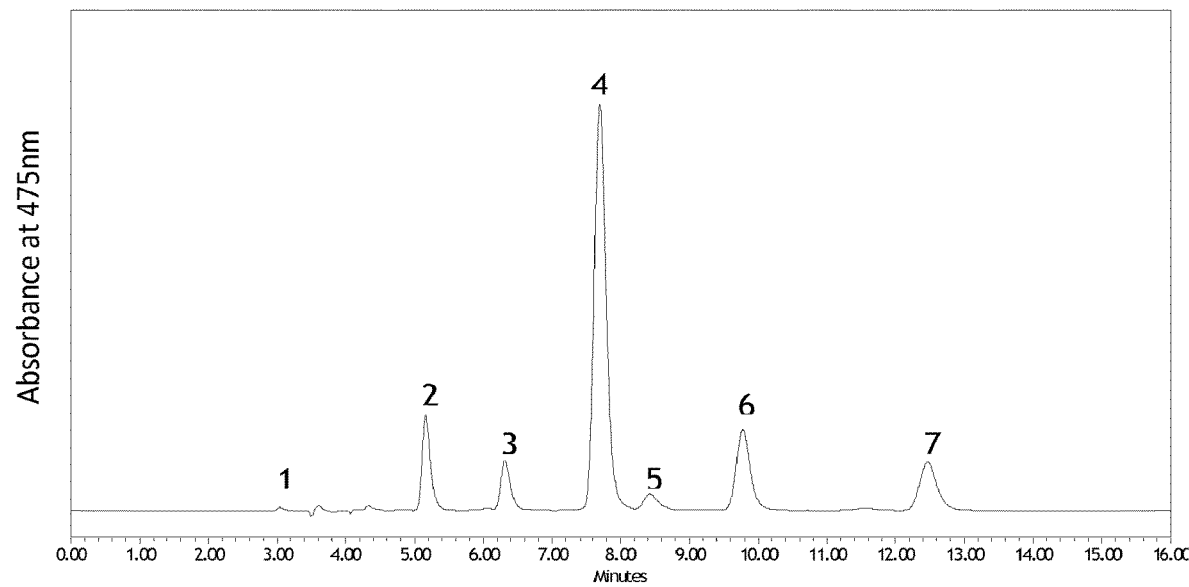

ACETYL TRANSFERASES AND THEIR USE FOR PRODUCING CAROTENOIDS

CROSS-REFERENCE TO RELATED APPLICATIONS

This application is a Divisional of application Ser. No. 14/650,298, filed Jun. 6, 2015, which is a U.S. National Phase of PCT/IB2013/058049, filed Aug. 28, 2013, which claims the benefit of U.S. Provisional Patent Application No. 61/830,234, filed Jun. 3, 2013, each of which is incorporated herein by reference in its entirety.

REFERENCE TO SEQUENCE LISTING SUBMITTED ELECTRONICALLY

The content of the electronically submitted sequence listing (Name: 4662_3873_Sequence_Listing.txt; Size: 50.2 kilobytes; and Date of Creation: Sep. 30, 2019) filed with the application is incorporated herein by reference in its entirety.

BACKGROUND OF THE INVENTION

The present invention relates to novel acetyl transferases, nucleic acid sequences coding therefore, expression constructs and vectors comprising these sequences, microorganisms transformed therewith and processes for the microbiological production of carotenoids, as for zeaxanthin, astaxanthin, lutein or β-cryptoxanthin.

Carotenoids are organic pigments ranging in color from yellow to red that are naturally produced by certain organisms, including photosynthetic organisms (e.g., plants, algae, cyanobacteria), and some fungi.

Carotenoids such as lutein, zeaxanthin or astaxanthin are important additives in the human and livestock diet as pigmenting substances and precursors of vitamin A derivatives. In addition, carotenoids have a health-promoting action such as enhancing the immune response and, by reason of their antioxidant properties, a cancer-preventing action, which makes their use as nutraceuticals of interest. An economic process for preparing carotenoids and foodstuffs with an increased carotenoid content is therefore of great importance. Particularly economic processes for preparing carotenoids are biotechnological processes which make use of proteins and biosynthesis genes of carotenoid biosynthesis from carotenoid-producing organisms.

SUMMARY OF THE INVENTION

The present invention is related to proteins or polypeptides, comprising the amino acid sequence SEQ ID NO:5, SEQ ID NO:6, SEQ ID NO:7, SEQ ID NO:8, or SEQ ID NO:14 respectively or a sequence derived from these sequences by substitution, insertion or deletion of amino acids and having a homology of at least 50% at the amino acid level with the sequence SEQ ID NO:5, SEQ ID NO:6, SEQ ID NO:7, SEQ ID NO:8 or SEQ ID NO:14. The inventors have surprisingly found that the incorporation of a gene encoding an acetyl transferase according to the invention into a host cell able to produce a specific carotenoid containing at least one hydroxyl group, as for example zeaxanthin or astaxanthin, alters carotenoid profiles in the host cells such that acetylated forms of the carotenoid are produced which allows an increased/enhanced accumulation of carotenoid compounds (acetylated plus non-acetylated forms) in the cell compared to strains not transformed with the gene encoding the protein or polypeptide according to the invention.

The present invention also relates to isolated polynucleotides encoding the polypeptides of the present invention, nucleic acid constructs, recombinant expression vectors, and recombinant host cells comprising the polynucleotides, and to methods of producing the polypeptides.

The present invention also provides improved systems, in particular transformed microorganisms for the biological production of carotenoids in which at least one heterologous polypeptide having acetyl transferase activity is expressed.

In one preferred example, the invention provides oleaginous fungi (including, for example, yeast) that produce one or more carotenoids. The present invention also provides methods of constructing such yeast and fungi, methods of using such yeast and fungi to produce carotenoids, and methods of preparing carotenoid-containing compositions, such as food or feed additives, or nutritional supplements, using carotenoids produced in such oleaginous yeast or fungi. In particular, the present invention provides systems and methods for generating yeast and fungi containing polynucleotides encoding the polypeptides of the present invention.

Overview of Sequence Listing

SEQ ID NO:1 is the non-optimized DNA sequence encoding acetyl transferase ATF1 from *S. cerevisiae*.
SEQ ID NO:2 is the non-optimized DNA sequence encoding acetyl transferase ATF1 from *S. bayanus*.
SEQ ID NO:3 is the non-optimized DNA sequence encoding acetyl transferase ATF1 from *S. mikatae*.
SEQ ID NO:4 is the non-optimized DNA sequence of acetyl transferase ATF1 from *S. kudriavzevii*.
SEQ ID NO:5 is the amino acid sequence as deduced from SEQ ID NO:1.
SEQ ID NO:6 is the amino acid sequence as deduced from SEQ ID NO:2.
SEQ ID NO:7 is the amino acid sequence as deduced from SEQ ID NO:3.
SEQ ID NO:8 is the amino acid sequence as deduced from SEQ ID NO:4.
SEQ ID NO:9 is the DNA sequence encoding acetyl transferase ATF1 from *S. cerevisiae* as optimized for expression in *Yarrowia lipolytica*.
SEQ ID NO:10 is the DNA sequence encoding acetyl transferase ATF1 from *S. bayanus* as optimized for expression in *Yarrowia lipolytica*.
SEQ ID NO:11 is the DNA sequence encoding acetyl transferase ATF1 from *S. mikatae* as optimized for expression in *Yarrowia lipolytica*.
SEQ ID NO:12 is the DNA sequence encoding acetyl transferase ATF1 from *S. kudriavzevii* as optimized for expression in *Yarrowia lipolytica*.
SEQ ID NO:13 is the non-optimized DNA sequence encoding acetyl transferase ATF1 from *S. arboricolus*.
SEQ ID NO:14 is amino acid sequence as deduced from SEQ ID NO:13.
SEQ ID NO:15 is the DNA sequence encoding acetyl transferase ATF1 from *S. arboricolus* as optimized for expression in Yarrowia lipolytica.
SEQ ID NO:16 is the DNA sequence encoding acetyl transferase ATF1 from *S. bayanus* as optimized for expression in *Paracoccus zeaxanthinifaciens* using *P. denitrificans* PD1222 codon usage table.

SEQ ID NO:17 is the DNA sequence encoding acetyl transferase ATF1 from *S. cerevisiae* as optimized for expression in *Paracoccus zeaxanthinifaciens* using *P. denitrificans* PD1222 codon usage table.

SEQ ID NO:18: is the non-optimized DNA sequence of acetyl transferase ATF1 from *S. cerevisiae* with an internal NdeI site removed.

BRIEF DESCRIPTION OF THE DRAWINGS

FIG. 3 shows zeaxanthin production of strain ML-13129 compared to ML-12218 (for construction, see Table 1 & 2) in a fed-batch fermentation (see Example 2c).

FIG. 4 shows astaxanthin production of strain ML-12819 compared to ML-12526 (for construction, see Table 1 & 2) in a fed-batch fermentation (see Example 2d).

FIG. 6 shows a typical chromatogram for zeaxanthin related compounds using HPLC (see Example 4).

FIG. 7 shows a typical chromatogram for astaxanthin related compounds using HPLC (see Example 4).

DEFINITIONS

Figures 1, 2:
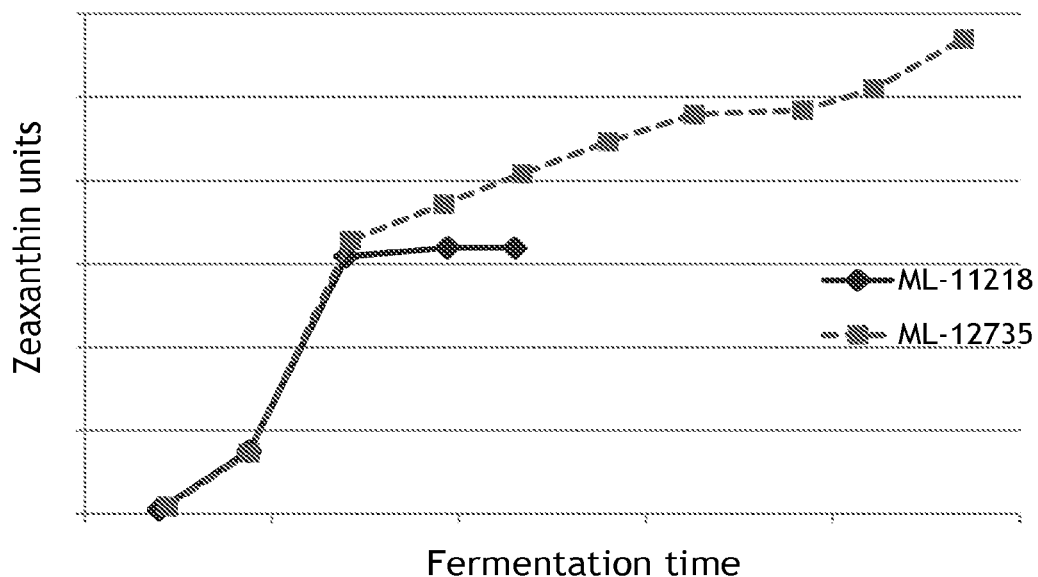
FIG. 1 shows zeaxanthin production of strain ML-12735 compared to ML-12218 (for construction, see Table 1 & 2) in a fed-batch fermentation (see Example 1b).
FIG. 2 shows astaxanthin production of strain ML-12707 compared to ML-12562 (for construction, see Table 1 & 2) in a fed-batch fermentation (see Example 1c).

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99% pure, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment–Total Number of Gaps in Alignment)

Fragment: The term "fragment" means a polypeptide having one or more (several) amino acids deleted from the amino and/or carboxyl terminus of a mature polypeptide; wherein the fragment has acetyl transferase activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, conjugation and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having acetyl transferase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Acetyl transferases hereinafter mean proteins or enzymes according to the invention which transfer an acetyl group to a carotenoid or carotenoid derivative containing at least one hydroxyl group, for example to zeaxanthin or astaxanthin, comprising the amino acid sequence SEQ ID NO:5, SEQ ID NO:6, SEQ ID NO:7, SEQ ID NO:8 or SEQ ID NO:14 or a sequence derived from these sequences by substitution, insertion or deletion of amino acids and having a homology of at least 50% at the amino acid level with the sequence SEQ ID NO:5, SEQ ID NO:6, SEQ ID NO:7, SEQ ID NO:8 or SEQ ID NO:14.

The amino acid sequence depicted in SEQ ID NO:5 is derived from translation of the cDNA sequence depicted in SEQ ID NO:1, the amino acid sequence depicted in SEQ ID NO:6 is derived from translation of the cDNA sequence depicted in SEQ ID NO:2, the amino acid sequence depicted in SEQ ID NO:7 is derived from translation of the cDNA sequence depicted in SEQ ID NO:3, the amino acid sequence depicted in SEQ ID NO:8 is derived from translation of the cDNA sequence depicted in SEQ ID NO:4, and the amino acid sequence depicted in SEQ ID NO:14 is derived from translation of the cDNA sequence depicted in SEQ ID NO:13.

Substitution means replacement of one or more amino acids by one or more amino acids. The replacements are preferably those called conservative, in which the replaced amino acid has a similar property to the original amino acid, for example replacement of Glu by Asp, Gln via Asn, Val by He, Leu by He, Ser by Thr.

Deletion is the replacement of an amino acid by a direct linkage. Preferred positions for deletions are the termini of the polypeptide and the linkages between the individual protein domains.

Insertions are introductions of amino acids into the polypeptide chain, there formally being replacement of a direct linkage by one or more amino acids.

The homology between two proteins means identity of the amino acids over the entire length of each protein, which is calculated by comparison with the aid of the computer program GAP (UWGCG, University of Wisconsin, Genetic Computer Group, program algorithm of Needleman and Wunsch (*J. Mol. Biol.* 1970, 48: 443-453), setting the following parameters:

Gap Weight: 12
Length Weight: 4
Average Match: 2.912
Average Mismatch: −2.003

A protein which has a homology of at least 50% at the amino acid level with the sequence SEQ ID NO:5, SEQ ID NO:6, SEQ ID NO:7, SEQ ID NO:8 or SEQ ID NO:14 means a protein which, in comparison of its sequence with the sequence SEQ ID NO:5, SEQ ID NO:6, SEQ ID NO:7, SEQ ID NO:8 or SEQ ID NO:14 using the above program algorithm with the above set of parameters, has an identity of at least 50%, preferably 60%, particularly preferably 70%.

The acetyl transferases can be prepared, as described hereinafter, by gene expression of the appropriate nucleic acids which encode these proteins from natural or genetically manipulated organisms.

The invention further relates to a process for transferring an acetyl group to a carotenoid or carotenoid derivative containing at least one hydroxyl group such as, for example, zeaxanthin, [beta]-cryptoxanthin, 3'-hydroxyechinenone, 3-hydroxyechinenone, adonixanthin (4-ketozeaxanthin), astaxanthin, phoenicoxanthin (adonirubin), [alpha]-cryptoxanthin or lutein or derivatives thereof having up to 40 C atoms. Preferably, such carotenoids or carotenoid derivatives contain at least one 3-hydroxy-[beta]-ionone or at least one 3-hydroxy-4-keto-[beta]-ionone or at least one 3-hydroxy-[epsilon]-ionone or at least one 3-hydroxy-4-keto-[epsilon]-ionone structural element in the molecule, such as, for example, 3-hydroxy-6-vinyl-[beta]-ionone, 3-hydroxy-4-keto-6-vinyl-[beta]-ionone, 3-hydroxyretinol, 3-hydroxy-4-ketoretinol, 3-hydroxyretinal, 3-hydroxy-4-ketoretinal, 3-hydroxyretinoic acid, 3-hydroxy-4-ketoretinoic acid or lutein.

The invention also relates to nucleic acid sequences coding for one of the acetyl transferases according to the invention. A preferred nucleic acid has the sequence SEQ ID NO:1, SEQ ID NO:2, SEQ ID NO:3, SEQ ID NO:4 or SEQ ID NO:13.

The invention moreover relates to functional analogs of the nucleic acids according to sequence SEQ ID NO:1, SEQ ID NO:2, SEQ ID NO:3, SEQ ID NO:4 or SEQ ID NO:13, obtained by addition, substitution, insertion and/or deletion of individual or multiple nucleotides, which furthermore code for an acetyl transferase having the desired specificity.

The invention also encompasses those nucleic acid sequences which comprise so-called silent mutations or which are modified in comparison with a specifically mentioned sequence in accordance with the codon usage of a specific origin or host organism, and naturally occurring variants of such nucleic acid sequences.

The invention also encompasses modifications of the nucleic acid sequences obtained by degeneration of the genetic code (i.e. without any changes in the corresponding amino acid sequence) or conservative nucleotide substitution (i.e. the corresponding amino acid is replaced by another amino acid of the same charge, size, polarity and/or solubility), and sequences modified by nucleotide addition, insertion, inversion or deletion, which sequences encode an acetyl transferase according to the invention having a "modified substrate profile", and the corresponding complementary sequences.

The invention furthermore relates to expression constructs comprising a nucleic acid sequence according to the invention under the genetic control of regulatory nucleic acid sequences; and vectors comprising at least one of these expression constructs.

The invention also relates to a recombinant nucleic acid molecule. "Recombinant nucleic acid molecule" primarily refers to a nucleic acid molecule or nucleic acid sequence comprises nucleic acid molecules from two or more different genetic sources. According to the present invention, the recombinant nucleic acid molecule can be an expression construct, i.e., nucleic acid sequence encoding the polypeptide having acetyl transferase according to the invention, operatively linked to an expression control sequence, or the same nucleic acid sequence being integrated into the host chromosome.

Preferably, the constructs according to the invention encompass a promoter 5'-upstream of the encoding sequence in question and a terminator sequence 3'-downstream, and, optionally, further customary regulatory elements, and, in each case operatively linked with the encoding sequence. Operative linkage is to be understood as meaning the sequential arrangement of promoter, encoding sequence, terminator and, if appropriate, other regulatory elements in such a manner that each of the regulatory elements can fulfill its intended function on expression of the encoding sequence. Examples of operatively linkable sequences are targeting sequences, or else translation enhancers, enhancers, polyadenylation signals and the like. Further regulatory elements encompass selectable markers, amplification signals, replication origins and the like.

In addition to the artificial regulatory sequences, the natural regulatory sequence can still be present upstream of the actual structural gene. If desired, this natural regulation may be switched off by genetic modification, and the expression of the genes may be enhanced or lowered. However, the gene construct may also be simpler in construction, i.e. no additional regulatory signals are inserted upstream of the structural gene and the natural promoter with its regulation is not removed. Instead, the natural regulatory sequence is mutated in such a way that regulation no longer takes place and the gene expression is increased or reduced. One or more copies of the nucleic acid sequences may be present in the gene construct. Examples of suitable promoters are: cos, tac, trp, tet, trp-tet, lpp, lac, lpp-lac, lacIq, T7, T5, T3, gal, trc, am, SP6, 1-PR or 1-PL promoter, which are advantageously employed in Gram-negative bacteria; and Gram-positive promoters amy and SPO2, the yeast promoters ADC1, MFa, Ac, P-60, CYC1, GAPDH, TEF1 or the plant promoters CaMV/35S, SSU, OCS, lib4, usp, STLS1, B33, nos or the ubiquitin or phaseolin promoter. Particular preference is given to using inducible promoters, for example light- and in particular temperature-inducible promoters, such as the PrP1 promoter.

In principle, all natural promoters with their regulatory sequences can be used. In addition, synthetic promoters may also be used in an advantageous fashion.

The above mentioned regulatory sequences are intended to allow the targeted expression of the nucleic acid sequences and of protein expression. Depending on the host organism, this may mean, for example, that the gene is expressed or over expressed only after induction has taken place, or that it is expressed and/or over expressed immediately and/or constitutively.

The regulatory sequences or factors can preferably have a positive effect on expression and in this manner increase or reduce the latter. Thus, an enhancement of the regulatory elements may advantageously take place at the transcriptional level by using strong transcription signals such as promoters and/or "enhancers". In addition, translation may also be enhanced by improving, for example, mRNA stability.

An expression cassette is generated by fusing a suitable promoter with a suitable acetyl transferase nucleotide sequence and a terminator signal or polyadenylation signal. To this end, customary recombination and cloning techniques are used as they are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987). For expression in a suitable host organism, the recombinant nucleic acid construct or gene construct is advantageously inserted into a host-specific vector which allows optimal gene expression in the host. Vectors are well known to the skilled worker and can be found, for example, in "Cloning Vectors" (Pouwels P. H. et al., Ed., Elsevier, Amsterdam-New York-Oxford, 1985). Vectors are to be understood as meaning not only plasmids, but all other vectors known to the skilled worker such as, for example, phages, viruses, such as SV40, CMV, baculovirus and adenovirus, transposons, IS elements, plasmids, cosmids, and linear or circular DNA. These vectors can be replicated autonomously in the host organism or chromosomally.

The vectors according to the invention allow the generation of recombinant microorganisms which are transformed, for example, with at least one vector according to the invention and which can be employed for producing the mutants. The above-described recombinant constructs according to the invention are advantageously introduced into a suitable host organism and expressed. It is preferred to use usual cloning and transfection methods known to the skilled worker in order to bring about expression of the abovementioned nucleic acids in the expression system in question. Suitable systems are described, for example, in current protocols in molecular biology, F. Ausubel et al., Ed., Wiley Interscience, New York 1997. Suitable host organisms are, in principle, all organisms which allow expression of the nucleic acids according to the invention, their allelic variants, and their functional equivalents or derivatives. Preferred initial organisms are those naturally able to synthesize carotenoids. However, initial organisms able to synthesize carotenoids because of the introduction of carotenoid biosynthesis genes are also suitable. Initial organisms mean prokaryotic or eukaryotic organisms such as, for example, microorganisms or plants. Preferred microorganisms are bacteria, yeasts, algae or fungi.

Therefore, the invention further relates to a process for preparing the genetically modified organisms described below, wherein the acetyl transferase genes according to the invention are introduced into the genome of the initial organism. By initial organisms are meant the organisms before the genetic modification according to the invention.

The acetyl transferase genes according to the invention can in principle be introduced by all methods known to the skilled worker into the initial organisms described below, which are genetically modified thereby.

They are advantageously introduced into the initial organisms or cells thereof by transformation, transfection, conjugation, electroporation, using the so-called particle gun, or by microinjection.

The skilled worker can find appropriate methods for microorganisms in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

Examples of advantageous methods which may be mentioned are those such as the introduction of the DNA by homologous or heterologous recombination, for example using the URA3 gene, specifically the URA3 gene from Ashbya, as described in the German Application DE 19801120.2, and/or by the REMI method (="restriction enzyme mediated integration") which is described below.

The REMI technique is based on the cotransformation of a linear DNA construct which has been cut at both ends with the same restriction endonuclease, together with the restriction endonuclease which was used for this restriction of the DNA construct, into an organism. The restriction endonuclease then cuts the genomic DNA of the organism into which the DNA construct has been introduced together with the restriction enzyme. This leads to an activation of the cell's own repair mechanisms. These repair mechanisms repair the strand breaks in the genomic DNA which have been caused by endonuclease, and during this also incorporate with a certain frequency the cotransformed DNA construct into the genome. Ordinarily, the restriction cleavage sites are retained at both ends of the DNA during this.

This technique was described by Bölker et al. (*Mol. Gen. Genet.* 1995, 248: 547-552) for the insertion mutagenesis of fungi. The method was used by Von Schiestl and Petes (*Proc. Natl. Acad. Sci. USA,* 1991, 88: 7585-7589) to find out whether there is heterologous recombination in *Saccharomyces*. The method has been described by Brown et al. (*Mol. Gen. Genet.* 1996, 251: 75-80) for the stable transformation and regulated expression of an inducible reporter gene.

It is possible using the REMI method to position the nucleic acid fragments according to the invention or the aforementioned acetyl transferase genes according to the invention at transcriptionally active sites in the genome.

It is possible and advantageous to clone the nucleic acids together with at least one reporter gene into a DNA construct, which is introduced into the genome. This reporter gene ought to make detectability easy by a growth, fluorescence, chemo- or bioluminesence assay or by a photometric measurement. Examples which may be mentioned of reporter genes are antibiotic resistance genes, hydrolase genes, fluorescent protein genes, bioluminescence genes, glucosidase genes, the luciferase gene, [beta]-galactosidase gene, gfp gene, lipase gene, esterase gene, peroxidase gene, [beta]-lactamase gene, acetyl-, phospho- or adenyltransferase gene. These genes make it possible easily to measure and quantify the transcription activity and thus the expression of the genes. This means that it is possible to identify sites in the genome which have a productivity differing by up to a factor of 2.

If it is intended to introduce a plurality of genes, such as, for example, further genes of carotenoid biosynthesis, into the organism, they can all be introduced together with a reporter gene in a single vector, or each individual gene with a reporter gene can be introduced in one vector in each case, into the organism, it being possible to introduce the various vectors at the same time or successively. It is also possible to insert gene fragments coding for the respective activities using the REMI techniques.

Restriction enzymes suitable in principle for integrating the acetyl transferase genes or nucleic acid constructs according to the invention into the genome of initial organisms are all known to the person skilled in the art. Restriction enzymes which recognize only 4 base pairs as restriction cleavage site are less preferred because they cut too often in the genome or in the vector to be integrated, and preferred enzymes recognize 6, 7, 8 or more base pairs as cleavage site, such as BamHI, EcoRI, BglII, SphI, SpeI, XbaI, XhoI, NcoI, SalI, ClaI, KpnI, HindIII, SacI, PstI, BpnI, NotI, SrfI or SfiI, to mention only a few of the possible enzymes. It is advantageous if the enzymes used no longer have cleavage sites in the DNA to be introduced; this increases the efficiency of integration. Ordinarily, 5 to 500 U, preferably 10 to 250, particularly preferably 10 to 100 U of the enzymes are used in the REMI mixture. The enzymes are advantageously employed in an aqueous solution which contains substances for osmotic stabilization, such as sugars such as sucrose, trehalose or glucose, polyols such as glycerol or polyethylene glycol, a buffer with an advantageous buffering in the range of pH 5 to 9, preferably 6 to 8, particularly preferably 7 to 8, such as tris, MOPS, HEPES, MES or PIPES and/or substances to stabilize the nucleic acids, such as inorganic or organic salts of Mg, Cu, Co, Fe, Mn or Mo. It is also possible where appropriate for other substances to be present, such as EDTA, EDDA, DTT, [beta]-mercaptoethanol or nuclease inhibitors. However, it is also possible to carry out the REMI technique without these additions.

The process is carried out at a temperature in the range from 5 to 80° C., preferably from 10 to 60° C., particularly preferably from 20 to 40° C. Other known methods for destabilizing cell membranes are suitable for the process, such as, for example, electroporation, fusion with loaded vesicles or destabilization with various alkali metal or alkaline earth metal salts such as lithium, rubidium or calcium salts, with lithium salts being preferred.

The invention further relates to a correspondingly genetically modified organism, with the expression of the acetyl transferase genes according to the invention being increased by comparison with a wild type organism in the case where the initial organism contains an acetyl transferase gene, or being caused in the case where the initial organism does not contain an acetyl transferase gene, by the genetic modification.

A genetically modified organism means an organism in which the acetyl transferase gene(s) or nucleic acid construct(s) according to the invention have been inserted, preferably by one of the methods described above.

The genetically modified organism contains at least one acetyl transferase gene according to the invention or at least one nucleic acid construct according to the invention. Depending on the initial organism, the nucleic acid may be present inside or outside the chromosome.

Carotenoid metabolism in the genetically modified organisms is preferably altered by comparison with the wild type.

Preferred organisms are recombinant bacteria, plants, fungi or yeast. In a particular embodiment, the recombinant fungus is oleaginous in that it can accumulate lipid to at least about 20% of its dry cell weight; and produces at least one carotenoid selected from the group consisting of antheraxanthin, adonirubin, adonixanthin, astaxanthin, canthaxanthin, capsorubrin, β-cryptoxanthin, α-carotene, δ-carotene, ε-carotene, echinenone, ζ-hydroxyechinenone, 3'-hydroxyechinenone, γ-carotene, ψ-carotene, 4-keto-γ-carotene, ζ-carotene, α-cryptoxanthin, □-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof, and can accumulate the produced carotenoid to at least about 1% of its dry cell weight. Even more preferably, the recombinant fungus is a member of a genus selected from the group consisting of: *Aspergillus, Blakeslea, Botrytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phaffia)*, and *Yarrowia*, or is of a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi (Gibberella zeae), Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullulans, Xanthophyllomyces dendrorhous (Phaffia rhodozyma)*, and *Yarrowia lipolytica*.

Of these naturally oleaginous strains, some also naturally produce carotenoids and some do not; these strains may be additionally utilized as a host cell by introduction of carotenoid biosynthesis genes as disclosed in U.S. Pat. No. 7,851,199.

In a particular embodiment, the recombinant bacterium is gram negative or positive. Gram-positive bacterial hosts include, but are not limited to, *Bacillus, Brevibacillus, Clostridium, Geobacillus, Lactobacillus, Lactococcus, Paenibacillus*, and *Streptomyces*. Gram-negative bacteria include, but are not limited to *E. coli, Pseudomonas* and *Paracoccus*.

The recombinant bacterial host may be any Bacillales including, but not limited to, *Bacillus amyloliquefaciens, Brevibacillus brevis, Bacillus circulans, Bacillus clausii, Bacillus coagulans, Bacillus lentus, Bacillus licheniformis, Geobacillus stearothermophilus, Bacillus subtilis*, and *Bacillus thuringiensis*. The recombinant bacterial host may also be any *Streptomyces* including, but not limited to, *Streptomyces achromogenes, Streptomyces avermitilis, Streptomyces coelicolor, Streptomyces griseus*, and *Streptomyces lividans*.

The recombinant bacterial host may also be any *Paracoccus* including, but not limited to *Paracoccus denitrificans, Paracoccus versutus, Paracoccus carotinifaciens, Paracoccus marcusii*, and *Paracoccus zeaxanthinifaciens*. The recombinant bacterium produces at least one carotenoid selected from the group consisting of antheraxanthin, adonirubin, adonixanthin, astaxanthin, canthaxanthin, capsorubrin, β-cryptoxanthin, α-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof.

In other embodiments, the present invention provides a method of producing a carotenoid, the method comprising steps of cultivating a fungus or bacterium under conditions that allow production of the carotenoid; and isolating the produced carotenoid.

Cultivation of the genetically modified organism according to the invention takes place in a manner known per se, such as cultivation of the appropriate wild type, for example in the case of microorganisms in a suitable medium such as, for example, on agar plates or in suspension culture, or in the case of plants in soil or appropriately suitable nutrient media. By harvesting is meant in the case of microorganisms the isolation of the microorganisms, and in the case of plants the cutting off of the plant or, where appropriate, particular plant parts containing the carotenoids. The carotenoids are isolated in a manner known per se, for example by disruption of the organism cells, extraction of the carotenoids and subsequent purification of the carotenoids by chemical or physical separation methods such as extraction or chromatography.

The following examples illustrate the invention.

EXAMPLES

Table 1 below describes certain *Yarrowia lipolytica* strains used in the following exemplification:

TABLE 1

*Yarrowia lipolytica* strains.

| Strain Number | Genotype | How Constructed |
|---|---|---|
| ML9863 | MATB erg9-4789::ura3 {HMG-tr GGS carB carRP crtW Xa-crtZ Dc-crtZ} prototrophic | Classical and standard molecular genetic techniques |
| ML9335 | MATA erg9-4789::ura3 {HMG-tr GGS carB carRP crtW Dc-crtZ} prototrophic | Classical and standard molecular genetic techniques |
| ML12526 | ML9335 plus extra copies of HMG-tr carB 3X-carRP | Untargeted transformations followed by removal of Hyg$^R$ and Nat$^R$ using cre-lox system |
| ML11218 | ML9863 crtW-Δ6180 | Targeted disruption with Hyg$^R$ cassette; subsequent marker removal using cre-lox system |

*Yarrowia* strains ML9863 and ML9335 were constructed by the introduction of heterologous genes under the control of constitutive promoters, coupled with several generations of crossbreeding, starting with ML350 and ATCC201249 as described in U.S. Pat. No. 7,851,199. The GGS gene and the truncated HMG gene ("HMG-tr") were derived from *Yarrowia* sequences corresponding to native geranylgeranyl pyrophosphate synthase and hydroxymethylglutaryl-CoA reductase genes, respectively. The carRP and carB genes were derived from *Mucor circinelloides*, and they encode a bifunctional phytoene synthase/lycopene cyclase and a phytoene dehydrogenase, respectively. The crtW gene was synthesized to encode the carotene ketolase of *Parvularcula bermudensis*. The crtZ gene was amplified from *Xanthobacter autotrophicus* (Xa), or synthesized to encode the carotene hydroxylase of *Cronobacter pulveris* (formerly known as *Enterobacter pulveris*) (Ep) or Enterobacteriaceae bacterium DC404 (Dc). These genes are sometimes but not always associated with auxotrophic markers (URA3, LEU2, URA2, LYS1, ADE1) or a loxP site, remnant of a Hyg$^R$ or Nat$^R$ marker.

TABLE 2

Plasmids.

| Plasmid | Backbone | Insert | Source |
|---|---|---|---|
| pMB6532 | pMB6157 (Hyg$^R$) | Sc-ATF1 | Synthesized NheI - MluI fragment |
| pMB6563 | pMB6532 | Sc-ATF1 (2$^{nd}$ copy) | Synthesized NheI - MluI fragment |

TABLE 2-continued

Plasmids.

| Plasmid | Backbone | Insert | Source |
|---|---|---|---|
| pMB6608 | pMB6563 | Nat$^R$ | pMB6200 |
| pMB6732 | pMB6157 | Sb-ATF1 | Synthesized NheI - MluI fragment |
| pMB6733 | pMB6157 | Sk-ATF1 | Synthesized NheI - MluI fragment |
| pMB6812 | pMB6157 | Sa-ATF1 | Synthesized NheI - MluI fragment |
| pMB6655 | pMB6157 | Hyg$^R$ | |
| pMB6674 | pMB6157 | Hyg$^R$ | |
| pMB6769 | pMB6655 | Sb-ATF1 | Synthesized NheI - MluI fragment |
| pMB6771 | pMB6674 | Sb-ATF1 | Synthesized NheI - MluI fragment |
| pMB6832 | pMB6771 (Hyg$^R$) | Sb-ATF1 - Sb-ATF1 | pMB6732 |
| pMB7006 | pRK415 | Tet$^R$ | Ref paper? |
| pMB6976 | pRK-PcrtE-crtE | Sb ATF1 (wild type) | Synthesized NdeI - HindIII fragment |
| pMB6977 | pRK-PcrtE-crtE | Sc-ATF1 (wild type with NdeI site in ORF removed) | Synthesized NdeI - HindIII fragment |
| pMB6978 | pRK-PcrtE-crtE | Sb-ATF1 | Synthesized NdeI - HindIII fragment |
| pMB6979 | pRK-PcrtE-crtE | Sc-ATF1 | Synthesized NdeI - HindIII fragment |

All basic molecular biology and DNA manipulation procedures described herein are generally performed according to Sambrook et al. or Ausubel et al. (J. Sambrook, E. F. Fritsch, T. Maniatis (eds). 1989. *Molecular Cloning: A Laboratory Manual*. Cold Spring Harbor Laboratory Press: New York; F. M. Ausubel, R. Brent, R. E. Kingston, D. D. Moore, J. G. Seidman, J. A. Smith, K. Struhl (eds.). 1998. *Current Protocols in Molecular Biology*. Wiley: New York).

Example 1a: Production of pMB6532, Encoding *S. cerevisiae* Acetyltransferase ATF1

The ATF1 gene of *Saccharomyces cerevisiae* was codon optimized according to *Yarrowia* codon bias, and the DNA fragment specified in SEQ ID No: 9 was synthesized de novo. During the de novo synthesis the sequence 5'-TGCTAGCCACAAAA, containing an NheI restriction site and a typical Kozak sequence for enabling efficient translation, was added immediately upstream of the ATG. The sequence ACGCGT-3', comprising an MluI restriction site, was added immediately downstream of the stop codon. This sequence was cleaved using NheI and MluI and ligated to pMB6157 cut with NheI and MluI to produce pMB6532. The resulting protein encoded by the Sc-ATF1 gene of pMB6532 is specified in SEQ ID No: 5. This plasmid was subsequently cleaved with EcoRV, and the Sc-ATF1-containing cassette duplicated by the insertion of a 2.35 kb SspI-PvuII fragment from the same plasmid, to create pMB6563, which encodes converging transcripts of Sc-ATF1 flanking a Hyg$^R$ marker. The Nat$^R$ marker, conferring nourseothricin resistance, was used to replace Hyg$^R$ in this plasmid by cleaving pMB6563 with SspI and BamHI and ligating it to the 1.3 kb SspI-BamHI fragment from pMB6200, to create pMB6608.

Example 1b: Introduction of *S. cerevisiae* Acetyltransferase ATF1 into a *Yarrowia* Strain Capable of Producing Zeaxanthin Strain ML11218 was transformed with a PvuII fragment of MB6563 comprising two copies of Sc-ATF1 under the control of constitutive promoters and a selectable marker for hygromycin resistance, Hyg$^R$. Ten hygromycin resistant transformants were chosen from the transformation plate (YPD+100 mg/L hygromycin) after 3-4 days of growth at 30° C. Most transformants produced between 14 and 17% of mono-acetylated Zeaxanthin and between 42 and 57% of di-acetylated zeaxanthin (as a percentage of total zeaxanthin) when grown in YPD for 4 days at 30° C. Free zeaxanthin production ranged between 27 and 42% of total zeaxanthin. One strain, ML12641, was chosen for further engineering.

Strain ML12641 was transformed with XbaI-treated MB6608, comprising two copies of Sc-ATF1 under the control of constitutive promoters and a selectable marker for nourseothricin, Nat$^R$. Ten nourseothricin resistant transformants were chosen from the transformation plate (YPD+100 mg/L nourseothricin) after 3-4 days of growth at 30° C. Several transformants produced between 9 and 16% monoacylated and between 56 and 80% di-acetylated zeaxanthin (as a percentage of total zeaxanthin) when grown in YPD for 4 days at 30° C. Free zeaxanthin production ranged between 11 and 28% of total zeaxanthin. One strain, ML12735, was chosen for further analysis and for cultivation in a fed-batch fermentor.

Strain ML12735 was grown in a fermentor using a fed-batch process. Total (free plus esterified) zeaxanthin production increased two-fold when compared to strain ML11218, which does not carry any copies of the Sc-ATF1 gene. Additionally, FIG. 1 illustrates that zeaxanthin production in strain ML11218 increases sharply early in the fermentation, then plateaus as zeaxanthin production ceases. In contrast, even though strain ML12735 has a similar production profile early in the fermentation process, zeaxanthin production continues to increase past the limit reached by ML11218, and the fermentation maintains its productivity for an extended period, unlike strain ML11218.

Example 1c: Introduction of *S. cerevisiae* Acetyltransferase ATF1 into a *Yarrowia* Strain Capable of Producing Astaxanthin Strain ML12526 was transformed with MB6563 (which contains converging transcripts of ATF1 flanking a Hyg$^R$ marker) that had been treated with XbaI. Five hygromycin resistant transformants were chosen from the transformation plate (YPD+100 mg/L hygromycin) after 3-4 days of growth at 30° C. After subsequent growth for 3-4 days in YPD shake flasks at 30° C., transformants produced between 22 and 29% of mono-acetylated and between 16 and 56% of di-acetylated astaxanthin (as a percentage of total astaxanthin). Free astaxanthin production ranged between 19 and 59% of total astaxanthin. One strain, ML12707, was chosen for further analysis and for cultivation in a fed-batch fermentor.

Strain ML12707 was grown in a fermentor using a fed-batch process. FIG. 2 illustrates that the rate of astaxanthin production in strain ML12707 is higher earlier in the fermentation and reaches a higher titer at the end of the run as compared to strain ML12562, which does not carry any copies of the Sc-ATF1 gene.

Example 2a: Production of pMB6732, pMB6733, and pMB6812, Encoding *S. bayanus, S. kudriavzevii*, and *S. arboricolus* Acetyltransferase ATF1, Respectively Plasmids were generated for the expression of ATF1 genes from different *Saccharomyces* species as described in Table 2. The ATF1 genes of *Saccharomyces bayanus* (Sb), *Saccharomyces kudriavzevii* (Sk), and *Saccharomyces arboricolus* (Sk) were codon optimized according to *Yarrowia* codon bias, and the DNA fragments specified in SEQ ID No: 10, 12, and 15, respectively, were synthesized de novo. During the de novo synthesis of the different ATF1 genes the sequence 5'-TGCTAGCCACAAAA, containing an NheI restriction site and a typical Kozak sequence for enabling efficient translation, was added immediately upstream of the ATG. The sequence ACGCGT-3', comprising an MluI restriction site, was added immediately downstream of the stop codon. The sequences were cleaved using NheI and MluI and ligated to pMB6157 cut with NheI and MluI to produce pMB6732, pMB6733, and pMB6812, respectively. The resulting proteins encoded by the ATF1 genes of pMB6732, pMB6733, and pMB6812 are specified in SEQ ID No: 6, 8, and 14, respectively.

Example 2b: Production of pMB6832, Harboring Two Copies of *S. bayanus* Acetyltransferase ATF1

*S. bayanus* ATF1 was also inserted as described above into two other vectors bearing constitutive promoters (pMB6655 and pMB6674), to create pMB6769 and pMB6771, and the two distinct cassettes were combined, via the transfer of a PvuII-SspI fragment from pMB6769 bearing one cassette into EcoRV-cleaved pMB6771, bearing the other cassette and a hygromycin resistant marker, to yield pMB6832.

Example 2c: Introduction of Acetyltransferase ATF1 Genes from *S. bayanus, S. kudriavzevii* and *S. arboricolus* into a *Yarrowia* Strain Capable of Producing Zeaxanthin Strain ML11218 was independently transformed with MB6732 (Sb-ATF1), MB6733 (Sk-ATF1) and MB6812 (Sa-ATF1) which had been treated with XbaI. Ten hygromycin resistant transformants of each plasmid were chosen from the transformation plate (YPD+100 mg/L hygromycin) after 3-4 days of growth at 30° C. After subsequent growth for 3-4 days in YPD shake flasks at 30° C., transformants were analyzed for zeaxanthin production and compared to the control strain, ML11218. Transformants harboring the *S. bayanus* ATF1 (pMB6732) produced between 4 and 16% mono-acetylated zeaxanthin and between 46 and 85% di-acetylated zeaxanthin (as a percentage of total zeaxanthin). Free zeaxanthin production ranged between 8 and 38% of total zeaxanthin. One transformant harboring *S. kudriavzevii* ATF1 (pMB6733) produced about 3% mono-acetylated zeaxanthin and no di-acetylated zeaxanthin (as a percentage of total zeaxanthin). Transformants harboring the *S. arboricolus* ATF1 (pMB6812) produced between 20 and 22% mono-acetylated zeaxanthin and between 30 and 45% di-acetylated zeaxanthin (as a percentage of total zeaxanthin). Free zeaxanthin production ranged between 34 and 49% of total zeaxanthin.

*S. bayanus* ATF1 was chosen for further studies and to investigate its acetylation capability in fermentors. Strain ML11218 was transformed with a PvuII fragment of pMB6832, harboring two copies of *S. bayanus* ATF1. Six hygromycin resistant transformants were chosen from the transformation plate (YPD+100 mg/L hygromycin) after 3-4 days of growth at 30° C. After subsequent growth for 3-4 days in YPD shake flasks at 30° C., transformants produced between 5 and 6% mono-acetylated zeaxanthin and between 83 and 90% di-acetylated zeaxanthin (as a percentage of zeaxanthin). Free zeaxanthin production ranged between 4 and 14% of total zeaxanthin. One strain, ML13129, was chosen for further analysis and for cultivation in a fed-batch fermentor.

Strain ML13129 was grown in a fermentor using a fed-batch process. Total (free plus esterified) zeaxanthin production increased 1.8-fold when compared to strain ML11218, which does not carry any copies of the Sb-ATF1 gene. Additionally, FIG. 3 illustrates that zeaxanthin production in both strains has a similar production profile early in the fermentation, but production in ML11218 plateaus and zeaxanthin production ceases. In contrast, zeaxanthin production continues to increase in strain ML13129 past the limit reached by ML11218 approaching almost double its levels.

Example 2d: Introduction of Acetyltransferase ATF1 Genes from *S. bayanus* and *S. kudriavzevii* into a *Yarrowia* Strain Capable of Producing Astaxanthin Strain ML12526 was independently transformed with MB6732 (Sb-ATF1) and MB6733 (Sk-ATF1) which had been treated with XbaI. Ten hygromycin resistant transformants of each plasmid were chosen from the transformation plate (YPD+100 mg/L hygromycin) after 3-4 days of growth at 30° C. After subsequent growth for 3-4 days in YPD shake flasks at 30° C., transformants were analyzed for astaxanthin production and compared to the control strain, ML12526. Transformants harboring the Sb-ATF1 plasmid pMB6732 produced between 16 and 30% mono acetylated astaxanthin and between 57 and 76% di acetylated astaxanthin (as a percentage of total astaxanthin). Free astaxanthin production ranged between 8 and 37% of total astaxanthin. Transformants harboring the Sk-ATF1 plasmid pMB6733 produced between 9 and 24% mono acetylated astaxanthin and between land 6% di acetylated astaxanthin (as a percentage of total astaxanthin). Free astaxanthin production ranged between 70 and 90% of total astaxanthin. One strain, ML12819, harboring the Sb-ATF1 plasmid pMB6732, was chosen for further analysis and for cultivation in a fed-batch fermentor. Strain ML12819 was grown in a fermentor using a fed-batch process. FIG. 4 illustrates that the rate of astaxanthin production in strain ML12819 is similar compared to strain ML12562, which does not carry the Sb-ATF1 gene, but reaches a higher titer at the end of the run.

Example 3a: Production of pMB6976, pMB6977, pMB6978 and pMB6979 Encoding Native and Codon Optimized *S. bayanus* and *S. cerevisiae* ATF1

*S. bayanus* and *S. cerevisiae* ATF1 genes were codon optimized for expression in *Paracoccus* sp. strain R114/pBBR-K-mev-op-R114-PcrtE-crtE$_{R114}$ (Patent US20070202579 A1, U.S. Pat. No. 7,232,679 B2) using the *Paracoccous denitrificans* PD1222 codon usage table, and the DNA fragments specified in SEQ ID No: 16 and SEQ ID No: 17, respectively, were synthesized de novo. Non codon optimized *S. bayanus* and *S. cerevisiae* ATF1 genes specified in the SEQ ID No: 2 and SEQ ID No: 18 were also synthesized de novo. The wild type *S. cerevisiae* ATF1 gene contains an NdeI site that was removed during de novo synthesis. During the de novo synthesis the sequence 5'-CAT was added immediately upstream of the ATG to create an NdeI restriction site. The sequence AAGCTT-3', comprising a HindIII restriction site, was added immediately downstream of the stop codon. Both codon optimized and non-codon optimized versions of *S. bayanus* and *S. cerevisiae* ATF1 were cloned under the control of the crtE promoter of *Paracoccus* using the plasmid pRK-PcrtE-crtE (derived from pRK415, Keen, et al., Gene. 1988, 70: 191-197) that had been cleaved with NdeI and HindIII to produce pMB6976 (Sb-ATF1 wild type), pMB6977 (Sc-ATF1 wild type), pMB6978 (Sb-ATF1 codon optimized) and pMB6979 (Sc-ATF1 codon optimized). The resulting protein encoded by the Sb-ATF1 genes in pMB6976 and pMB6978 is specified in SEQ ID No: 6. The resulting protein encoded by the Sc-ATF1 genes in pMB6977 and pMB6979 is specified in SEQ ID No: 5.

Table 3 below describes the *E. coli* strains used in the following exemplification:

TABLE 3

*E. coli* strains.

| Strain | Gene introduced | How constructed |
|---|---|---|
| MB7006 | none | Transformation |
| MB7007 | Sb-ATF1 (wild type) | Transformation |
| MB7008 | Sc-ATF1 (wild type) | Transformation |
| MB7009 | Sb-ATF1 (codon optimized) | Transformation |
| MB70010 | Sc-ATF1 (codon optimized) | Transformation |

Table 4 below describes the *Paracoccus* strains used in the following exemplification:

TABLE 4

*Paracoccus zeaxanthinifaciens* strains.

| Strain | Gene introduced | How constructed |
|---|---|---|
| R114/pBBR-K-mev-op-R114-PcrtE-crtE$_{R114}$ + pMB7006 | none | Conjugation with MB7006 (Rif$^R$ and Tet$^R$ selection) |
| R114/pBBR-K-mev-op-R114-PcrtE-crtE$_{R114}$ + pMB7007 | Sb-ATF1 wild type | Conjugation with MB7007 (Rif$^R$ and Tet$^R$ selection) |
| R114/pBBR-K-mev-op-R114-PcrtE-crtE$_{R114}$ + pMB7008 | Sc-ATF1 wild type | Conjugation with MB7008 (Rif$^R$ and Tet$^R$ selection) |
| R114/pBBR-K-mev-op-R114-PcrtE-crtE$_{R114}$ + pMB7009 | Sb-ATF1 codon optimized | Conjugation with MB7009 (Rif$^R$ and Tet$^R$ selection) |
| R114/pBBR-K-mev-op-R114-PcrtE-crtE$_{R114}$ + pMB7010 | Sc-ATF1 codon optimized | Conjugation with MB7010 (Rif$^R$ and Tet$^R$ selection) |

Example 3b: Introduction of *S. bayanus* and *S. cerevisiae* ATF1 into a *Paracoccus* Strain Capable of Producing Zeaxanthin Via Conjugation Plasmid pMB6975 (pRK415 control plasmid) and plasmids pMB6976, pMB6977, pMB6978 and pMB6979 harboring the different ATF1 genes were transformed into *E. coli* strain S17-1 to produce strains MB7706, MB7007, MB7708, MB7709 and MB7710. *E. coli* strain S17-1 is a mobilization host containing transfer genes in its chromosome. The vector pRK415 is used as the expression plasmid and harbors the transfer genes necessary to move it into *Paracoccus*. Plasmids pMB6975-pMB6979 were individually introduced into *Paracoccus* sp. strain R114/pBBR-K-mev-op-R114-PcrtE-crtE$_{R114}$ (Rif$^R$) via conjugation with *E. coli* strains MB7706-MB7710 and selection on 100 mg/L rifampicin and 2.5 mg/L tetracycline. The *Paracoccus* exconjugants created were named R114/pBBR-K-mev-op- R114-PcrtE-crtE$_{R114}$+pMB7006, R114/pBBR-K-mev-op-R114-PcrtE-crtE$_{R114}$+pMB7007, R114/pBBR-K-mev-op-R114-PcrtE-crtE$_{R114}$+pMB7008, R114/pBBR-K-mev-op-R114-PcrtE-crtE$_{R114}$+pMB7009, and R114/pBBR-K-mev-op-R114-PcrtE-crtE$_{R114}$+pMB7010. Six *Paracoccus* exconjugants harboring the different ATF1 genes and six exconjugants harboring the control plasmid were selected and grown on F-medium (10 g/l tryptone, 10 g/l yeast extract, 30 g/l NaCl, 10 g/l D-glucose, 5 g/l MgSO4.7H2O, pH 7.0) at 28° C. at 200 rpm for 24 hours and analyzed for carotenoid production. One milliliter of broth was harvested, spun down, and the cell pellet was extracted for carotenoids as described for *Yarrowia lipolytica* samples. All *Paracoccus* strains harboring optimized and non-optimized *S. bayanus* and *S. cerevisiae* ATF1 genes produced acetylated zeaxanthin and β-cryptoxanthin in addition to free zeaxanthin, β-cryptoxanthin, and carotenes. The control strain, R114/pBBR-K-mev-op-R114-PcrtE-crtE$_{R114}$+pMB7006, without ATF1, does not produce acetylated zeaxanthin or acetylated β-cryptoxanthin.

Figure 5:
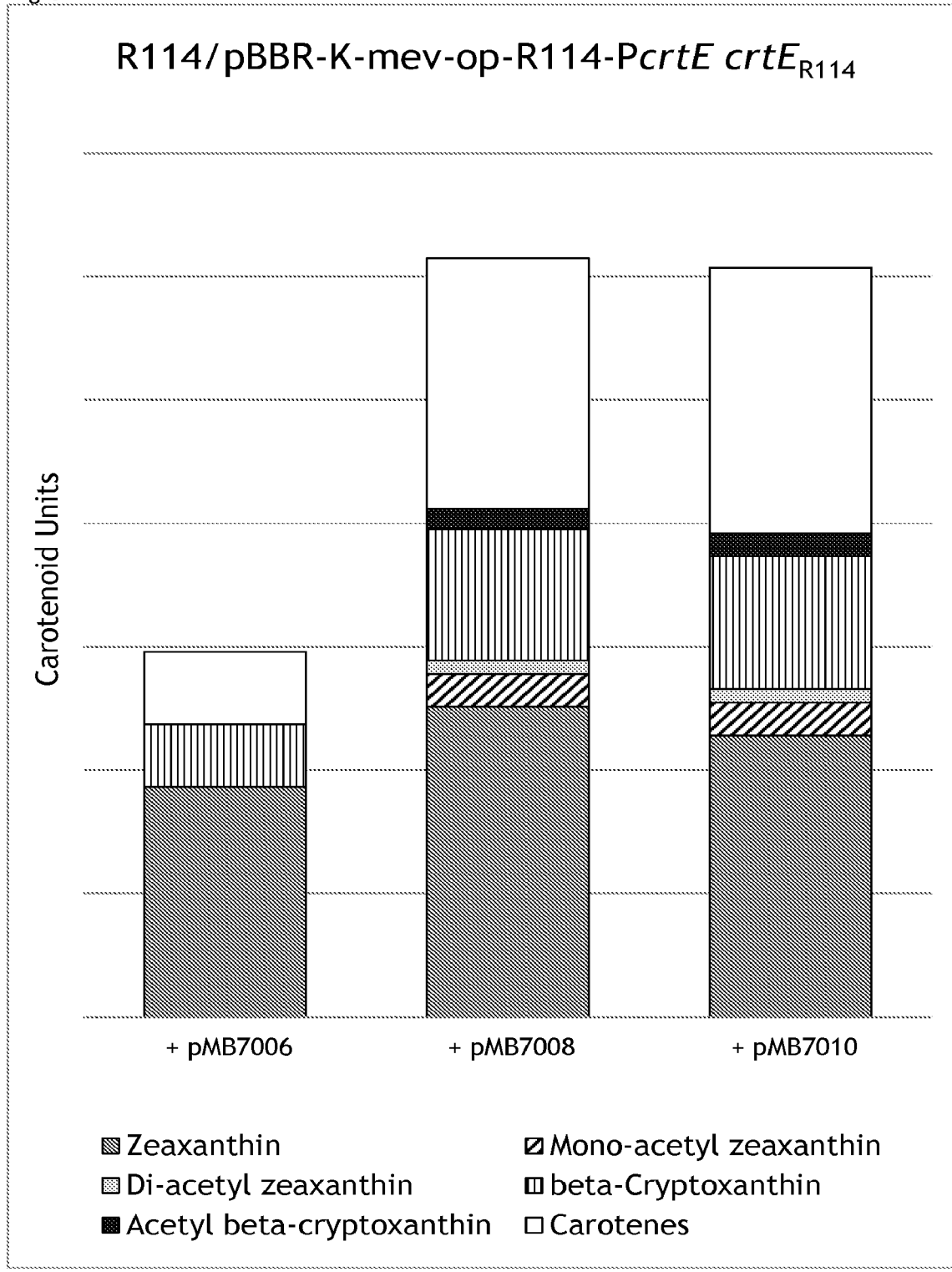
FIG. 5 shows production of mono-acetylated zeaxanthin, di-acetylated zeaxanthin, free zeaxanthin, β-cryptoxanthin, acetyl beta-cryptoxanthin, carotenes of 3 different *Paracoccus zeaxanthinifaciens* strains (for construction, see Table 4) grown in F-medium (see Example 3b).

Two typical *Paracoccus* exconjugants, R114/pBBR-K-mev-op-R114-PcrtE-crtE$_{R114}$+pMB7008-11 and R114/pBBR-K-mev-op-R114-PcrtE-crtE$_{R114}$+pMB7010-9, harboring the wild type and the codon optimized ATF1 gene from *S. cerevisiae*, respectively, were chosen for more detailed analysis and comparison to the control strain, R114/pBBR-K-mev-op-R114-PcrtE-crtE$_{R114}$+pMB7006-10. Strains were grown on F-medium as described above. Five hundred microliters of whole broth were harvested and lyophilized for 48 hours. Carotenoids were extracted and analyzed as described for *Yarrowia lipolytica* samples. FIG. 5 shows that AM-harboring strains produced about 10% mono-acetylated and about 4% di-acetylated zeaxanthin (as a percentage of total zeaxanthin. The ATF1-harboring strains also produced 74% and 65% more hydroxylated product (acetylated and free zeaxanthin, and β-cryptoxanthin) than the control strain (55% and 43% more total zeaxanthin).

Example 4: Extraction and Quantification of Carotenoid Production by HPLC from *Yarrowia lipolytica* and *Paracoccus* Cells Shake flask testing and carotenoid analysis of generated strains were performed according to the methods described previously in U.S. Pat. No. 7,851,199 B2.

For quantification of acetylated carotenoids from *Yarrowia* and *Paracoccus* by HPLC and HPLC DAD MS the following methods were used:

Normal Phase Carotenoid Method

A Waters 1525 binary pump attached to a Waters 717 auto sampler was used to inject samples. A Phenomenex Luna 3μ Silica (2), 150×4.6 mm column with a security silica guard column kit was used to resolve carotenoids. Synthetic carotenoid samples, purchased from CaroteNature (GmbH, Im Budler 8, CH-4419 Lupsingen, Switzerland) or received from DSM Nutritional Products Ltd., were used as reference standards. Acetylated compounds of astaxanthin and zeaxanthin were synthesized based on experiments reviewed in Kaewkoola and Krisnangkura, *Chem Phys Lipids*. 2010, 163: 685-688 and Kaewkool, et al., *Eur. J. Lipid Sci. Technol*. 2009, 111: 474-480. Approximately, 100 mg/L of carotenoid was dissolved in ethyl acetate and excess base of either sodium hydroxide or potassium hydroxide was added. Samples were allowed to sit in dark at room temp and analyzed periodically from 1-5 days. Synthesized acetylated components were then used as retention time markers, but quantitation is based on non-acetylated compound. All other acetylated compounds, except from zeaxanthin and astaxanthin, were identified by UV spectral features only. The mobile phase consisted of 1000 mL hexane, 30 mL isopropanol, and 0.1 mL acetic acid for astaxanthin-related compounds, or 1000 mL hexane, 60 mL isopropanol, and 0.1 mL acetic acid for zeaxanthin-related compounds. The flow rate for each run was 0.6 mL per minute. Column temperature was ambient. The injection volume was 20 μL. The detector was a photodiode array detector collecting from 210 to 600 nm.

A typical chromatogram for zeaxanthin related compounds using this method is shown in FIG. 6:
 1: carotenes
 2: acetylated β-cryptoxanthin
 3: di-acetylated zeaxanthin
 4: β-cryptoxanthin
 5: mono-acetylated zeaxanthin
 6: zeaxanthin A typical chromatogram for astaxanthin related compounds using the above method is shown in FIG. 7:
 1: carotenes
 2: di-acetylated adonixanthin
 3: mono-acetylated adonixanthin
 4: di-acetylated astaxanthin
 5: adonirubin
 6: mono-acetylated astaxanthin
 7: astaxanthin HPLC DAD MS Method For determination of acetylated zeaxanthin by HPLC DAD MS, samples were re-suspended in ice cold extraction solvent (50/50 v/v mix of hexane and ethyl acetate containing 0.01% butyl-hydroxy-toluene (BHT). An Alliance 2795 HPLC (Waters) system equipped with a Waters X-Bridge C18 column (3.5 μm, 2.1×50 mm) and a Thermo Basic 8 guard column (2.1×10 mm) was used to resolve carotenoids at 25° C. Authentic carotenoid samples were used as standards. The mobile phase and flow rates are shown below (Solvent A=Ethyl Acetate; Solvent B=Water; Solvent C=Methanol; Solvent D=Acetonitrile). The injection volume was 10 μL. The detector was a Waters 996 photodiode array detector in tandem with a Micro Mass Quattro Micro mass spectrometer. The mass spectrometer was run in default settings for single ion monitoring in positive ion mode. The cone voltage used was 35V. The retention time for zeaxanthin was 1.09 minutes, maximum absorbance at 450 nm with mono isotopic mass 569.4 in positive ion mode. The retention time of the mono-acetylated zeaxanthin was 2.68 minutes, maximum absorbance at 450 nm with mono isotopic mass 611.4 in positive ion mode. The retention time of the di-acetylated zeaxanthin was 3.08 minutes, maximum absorbance at 450 nm with mono-isotopic mass 653.4 in positive ion mode. The retention time for other carotenoids was: β-cryptoxanthin, 3.2 minutes, lycopene, 3.6 minutes, □-carotene, 3.8 minutes and β-carotene, 3.95 minutes.

| Flow Rate and Mobile Phase Gradient | | | | | | |
|---|---|---|---|---|---|---|
| Time (min) | Flow (mL/min) | % A | % B | % C | % D | Curve |
| 0.0 | 0.5 | 0 | 20 | 0 | 80 | 6 |
| 3.0 | 1.0 | 20 | 0 | 0 | 80 | 6 |
| 4.5 | 1.0 | 80 | 0 | 20 | 0 | 6 |
| 5.0 | 0.9 | 0 | 0 | 100 | 0 | 6 |
| 6.0 | 0.9 | 0 | 0 | 100 | 0 | 6 |
| 6.5 | 0.9 | 0 | 20 | 0 | 80 | 6 |
| 7.0 | 0.5 | 0 | 20 | 0 | 80 | 6 |

The invention claimed is:

1. A process for conversion of at least one carotenoid selected from the group consisting of zeaxanthin, astaxanthin, lutein, and beta-cryptoxanthin, containing at least one ring-associated hydroxyl-group, into the corresponding partially or fully acetylated carotenoid molecule, comprising using a carotenoid-producing oleaginous fungus or bacterium which has been transformed with a polynucleotide encoding at least one heterologous enzyme having acetyl transferase activity and expresses said enzyme, wherein said enzyme comprises the amino acid sequence of SEQ ID NO:6.

2. The process according to claim 1, wherein the oleaginous carotenoid-producing fungus is selected from *Yarrowia*.

3. The process according to claim 1, wherein the oleaginous carotenoid-producing bacterium is selected from *Paracoccus*.

4. The process according to claim 1, wherein the polynucleotide encoding said enzyme comprises a nucleotide sequence selected from the group consisting of SEQ ID NO: 2, 10, and 16.

5. The process according to claim 2, wherein the oleaginous carotenoid-producing fungus is *Yarrowia lipolytica*.

6. The process according to claim 3, wherein the oleaginous carotenoid-producing bacterium is *Paracoccus zeaxanthinifaciens*.

* * * * *

SEQUENCE LISTING

<160> NUMBER OF SEQ ID NOS: 18

<210> SEQ ID NO 1
<211> LENGTH: 1578
<212> TYPE: DNA
<213> ORGANISM: Saccharomyces cerevisiae

<400> SEQUENCE: 1

| | | |
|---|---|---|
| atgaatgaaa tcgatgagaa aaatcaggcc cccgtgcaac aagaatgcct gaaagagatg | 60 |
| attcagaatg ggcatgctcg gcgtatggga tctgttgaag atctgtatgt tgctctcaac | 120 |
| agacaaaact tatatcgaaa cttctgcaca tatggagaat tgagtgatta ctgtactagg | 180 |
| gatcagctca cattagcttt gagggaaatc tgcctgaaaa atccaactct tttacatatt | 240 |
| gttctaccaa caagatggcc aaatcatgaa aattattatc gcagttccga atactattca | 300 |
| cggccacatc cagtgcatga ttatatttca gtattacaag aattgaaact gagtggtgtg | 360 |
| gttctcaatg aacaacctga gtacagtgca gtaatgaagc aaatattaga agaattcaaa | 420 |
| aatagtaagg gttcctatac tgcaaaaatt tttaaactta ctaccacttt gactattcct | 480 |
| tactttggac aacaggacc gagttggcgg ctaatttgtc ttccagaaga gcacacagaa | 540 |
| aagtggaaaa aatttatctt tgtatctaat cattgcatgt ctgatggtcg gtcttcgatc | 600 |
| cactttttc atgatttaag agacgaatta aataatatta aaactccacc aaaaaaatta | 660 |
| gattacattt tcaagtacga ggaggattac caattattga ggaaacttcc agaaccgatc | 720 |
| gaaaaggtga tagactttag accaccgtac ttgtttattc cgaagtcact tctttcgggt | 780 |
| ttcatctaca atcatttgag attttcttca aaaggtgtct gtatgagaat ggatgatgtg | 840 |
| gaaaaaaccg atgatgttgt caccgagatc atcaatattt caccaacaga atttcaagcg | 900 |
| attaaagcaa atattaaatc aaatatccaa ggtaagtgta ctatcactcc gttttttacat | 960 |
| gtttgttggt ttgtatctct tcataaatgg ggtaaatttt tcaaaccatt gaacttcgaa | 1020 |
| tggcttacgg atattttat ccccgcagat tgccgctcac aactaccaga tgatgatgaa | 1080 |
| atgagacaga tgtacagata tggcgctaac gttggattta ttgacttcac ccctggata | 1140 |
| agcgaatttg acatgaatga taacaaagaa aatttttggc cacttattga gcactaccat | 1200 |
| gaagtaattt cggaagcttt aagaaataaa aagcatctcc atggcttagg gttcaatata | 1260 |
| caaggcttcg ttcaaaaata tgtgaacatt gacaaggtaa tgtgcgatcg tgccatcggg | 1320 |
| aaaagacgcg gaggtacatt gttaagcaat gtaggtctgt ttaatcagtt agaggagccc | 1380 |
| gatgccaaat attctatatg cgatttggca tttggccaat tcaaggatc ctggcaccaa | 1440 |
| gcattttcct tgggtgtttg ttcgactaat gtaaagggga tgaatattgt tgttgcttca | 1500 |
| acaaagaatg ttgttggtag tcaagaatct ctcgaagagc tttgctccat ttacaaagct | 1560 |
| ctccttttag gcccttag | 1578 |

<210> SEQ ID NO 2
<211> LENGTH: 1578
<212> TYPE: DNA
<213> ORGANISM: Saccharomyces bayanus

<400> SEQUENCE: 2

| | | |
|---|---|---|
| atgaatacct atagtgaaaa aacctctctt gttcaagacg aatgtctggc aaagatgata | 60 |
| cagaatgggc attcgcggcg tatgggatcc gtcgaagact tgtacgctgc cctcaacaga | 120 |
| cagaaactgt atcggaattt ctcgacatat tcagagctga atgattactg caccaaagat | 180 |
| caactcgcat tagctctaag aaatatatgt ttgaaaaatc caactcttct acatattgtg | 240 |

```
ttaccggcaa gatggccaga tcatgaaaat tattacctta gctcagaata ttattcacag      300
ccacatccaa aacatgatta tatctcagtt ttgcctgagt taaaattcga tggtgtgatt      360
ctcaatgagc aacctgagca caatgcccta atgaagcaaa tacttgaaga acttaaggat      420
agcaatggat cttatactgc gaaaatcttc aaattgacca ccgctttgac tattccatac      480
gctgggccaa caagtccgac ttggcggctg atttgtcttc agaagaagg atacacagat       540 aagtggaaga aatttatatt tctatccaat cactgcatgt gtgatggtag aacctcaatt      600 cacttttttcc aggatctaag agatgaatta acaatatca aaactccgcc aaagaaattg     660
gactacattt tccagtacga aaaggactac caacttttga aaagctccc agaaccaatt      720 gaaaatatga tagatttttag gccacccctat atgtttattc cgaagtccct tatttcgggc  780
ttcatttaca gtcatttgag gttctcttca aagggtgtgt gcacgagaat ggatgagtta     840
gaaaagaatg atgatattgt tacagaaatc atcaccatct caccatcaga acttcaaaaa    900
attagaacga aaatcaaatc aaacattcca ggcaagtgca ccatcactcc gttcttagaa    960
gtttgttggt ttgtatctct ccataagtgg ggcaagtttt tcaaaccatt gaagttcgag   1020
tggcttaccg atgttttttat tcctgcagat tgccgctcat tgctgcctga agatgaagat  1080
gtgagagcta tgtacaggta cggcgctaac gtcgggtttg ttgacttcac tccatggata  1140
agcgaattta acatgaatga cagcaaagaa aatttctggc cacttatagc acattatcat   1200
gaagtaattt caggggcgat aaatgacaag aagcatctca atggtttggg gttcaatata  1260
caaggcttgg tccaaaagta tgtcaacatt gacaaagtaa tgcgcgatcg tgctcttggt   1320
aaatcacgcg gaggtacgtt gttgagtaac gtgggtatttt ccatcaatc ggaggagacc  1380 gacagtagat attcaataag agatttggca ttcggtcaat ttcaagggtc atggcatcaa   1440
gcattttcat tgggtgtttg ttcgactaat gtgaagggaa tgaacattgt aatttcttca   1500
acgaaaaatg ccgtgggtag ccaagaattg ttggaggaac tttgtgccat gtacaaggct   1560
ctgttgttag atccttaa                                                  1578
```

<210> SEQ ID NO 3
<211> LENGTH: 1575
<212> TYPE: DNA
<213> ORGANISM: Saccharomyces mikatae

<400> SEQUENCE: 3

```
atgaatgaac taactgagaa acatatccca gttcaacatg aatgtctgga aaagatgata       60
cagaatgggc acgctcggcg aatgggatca gttgaggatc tttatgttgc cctcaacaga     120
caaaacttat atcggaactt ttcgacatat gctgaactaa ccgattactg tactagggat     180
cagcttacac tagctttgag ggagttatgc ttaaagaatc caaccctttt gcacattgtg     240
ttacccacaa gatggccaaa tcatgaaact tattaccgta gctcagaata ttattcacgg     300
cctcacccaa aacatgatta catttcagtt ttacaagaat tgaagctgga cggtgtggtt     360
ctcaatgatc aacctcagta tagtgcaatt atgaagcaaa tattggaaga attcaagaat    420
agtaatggta cttatactgc gaaaatcttt aaatacacta ccaaattgac tattccttac    480
ttcggaccaa atggtcccaa ttggcggcta atctgtcttc agaagaaca tacagataga    540 tggaagaaat ttatctttgt ctctaatcac tgcatgtctg atggtagatc ttcgattcac   600
ttttttcatg atctaaggga tgaattaaat aggatcaaaa ctccgccaag aaaaacagac   660 tacatttttcc agtatgaaag cgactatcaa ttgttaagaa agcttccaga accaatcgaa  720
```

```
agggtgatag actttaggcc accatatttg tttattccaa agtcccttttt ttcgggattc    780
atctataatc atttaaggtt ttcttcaaag ggtatttgta tgagaatgga agatatggaa    840
aagtgtgatg acgttgttac cgacattatc actattacac catcagaact tcaagaaatt    900
agagcaaaaa taaaactaaa tattcaaggc aagtgtacca tcacgccatt tttacaggtt    960
tgttggtttg tatctcttca taaatggggc aagttttttca agccgctgaa ctttgagtgg   1020
ctcacggata tttttattcc cgcagattgc cgttcagaac taccggatga tgaagaagtg   1080
aggcagatgt atagatatgg cgctaatgtt gggtttgttg acttcacccc gtggataagt   1140
gaattcgata tgaatgacag tgaagaaaac ttttggcccc ttattaaaca ctaccatgaa   1200
gtaatttcag ccgccctaaa agataagaaa caccttcatg ggttggggtt taacatacaa   1260
ggcttcgtcc aaaaatatgt gaatattgac aaggcaatgt gtgatcgtgc cattggaaaa   1320
gcacgtggtg gtaccttgtt gagtaatgtt ggtatgttca atcaagtgaa ggagccggac   1380
accaaatatt ctataaggga cttggcgttt ggtcaatttc aggggtcgtg gcatcaagca   1440
ttttcattag gcgtttgttc gactaatgtg aaggggatga acattcttgt agcttcaacc   1500
aaaaatgttg tgggcagtca agaatcgttg gaagaacttt gctccatttt caagtctctg   1560
cttttaggaa cctag                                                    1575

<210> SEQ ID NO 4
<211> LENGTH: 1575
<212> TYPE: DNA
<213> ORGANISM: Saccharomyces kudriavzevii

<400> SEQUENCE: 4
atgactaaaa tcagcgaaga gcactttcct attcaacatg aatgtctgga aaggatgatt     60
cagaatgggc atgctcggcg tatgggatca gttgaagact tgtacgtggc cctcaacaga    120
caaaaattgt atcgaaactt ttcagcatat gcggaactaa gtgattactg tagcaaggat    180
cagctaacat tagcgctgag aaatatatgt ttgaaaaatc caactctttt gcacattgta    240
ttaccaacaa gatggccaga tcatgaaaac tattatctca gctcggaata ttattcacac    300
ccacatcctg aacatgatta tatctcggtt ttaccagaat aaaaactaga tggtgtaatt    360
atcaatgaac aacctgaaaa cggtaagata gtgaggcaaa tattggaaga gttcaggaac    420
agcaatggta cttataatgc aaaaatcttt aaattgacta ccgctttgac cattccttac    480
tttgggccaa caagtccaaa ttggcggcta atttgtctcc cagaggagca cacagataag    540
tggaaaaaat tcatatttgt atctaatcac tgcatgtccg atggtagatc ttcaattcac    600
ttttttcatg atctaaaagc cgaattaaat gatatcaaaa ccccaccaaa gaaattggac    660
tatcttttca aatacgaaaa tgattatcaa ttattaagaa aacttccaga gccaattgaa    720
aaggtgatag atttcagacc accatatctg tttattccaa aatctcttct ttcaggattt    780
atttataatc acttgagatt tgcttcaagg ggcatatgca caagaatgga tgatatggaa    840
aaaagtgacg atgttgttgc agaaatcatc actatttcac catcagaact acaagaaatt    900
aggaccaaaa tcaaatcaaa cattcaaggc aagtgtactc tcacgccatt tttgcaagtt    960
tgttggtttg tgtctcttca tcaatggggc aagttttttca aaccattgaa ctttgagtgg   1020
cttactgata tcttcattcc cgcagattgc cgtccacaac tacctgatga tgaagaagtg   1080
aggcagatgt acaggtatgg cgctaacgtg gggtttgttg atttcactcc gtggatatgc   1140
gagtctaata tgaatgacaa caaagaaaat ttttggccac ttatcgaaca ttaccatcag   1200
gtaatttctg gggctctaag agacaataaa caccttcatg gcttagggct caatatacaa   1260
```

```
ggctttgtcc aaaaatacgt caatattgat aaggcaatgt gcgatcgtgc tatcggaaag    1320
gcacgtggag gtacattgtt gagtaatgta ggtatgttta agcagttgga ctcgtccaac    1380
tgcaactatt ctataaaaga cttggctttt gggcaatttc aagggtcatg caccaagca     1440 ttttcattgg gtgtttgttc gactgatgta aaggaatga atattattgt tgcatcaaca     1500
aaaaacgttg ttggtagcca ggaatcgttg gaagaacttt gccgcgtcta caaggctatg    1560
cttttaggac cctag                                                     1575
```

<210> SEQ ID NO 5
<211> LENGTH: 525
<212> TYPE: PRT
<213> ORGANISM: Saccharomyces cerevisiae

<400> SEQUENCE: 5

```
Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
            20                  25                  30

Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
            100                 105                 110

Gln Glu Leu Lys Leu Ser Gly Val Val Leu Asn Glu Gln Pro Glu Tyr
        115                 120                 125

Ser Ala Val Met Lys Gln Ile Leu Glu Glu Phe Lys Asn Ser Lys Gly
    130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
            180                 185                 190

Met Ser Asp Gly Arg Ser Ser Ile His Phe His Asp Leu Arg Asp
        195                 200                 205

Glu Leu Asn Asn Ile Lys Thr Pro Pro Lys Lys Leu Asp Tyr Ile Phe
    210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
            260                 265                 270

Val Cys Met Arg Met Asp Asp Val Glu Lys Thr Asp Asp Val Val Thr
        275                 280                 285

Glu Ile Ile Asn Ile Ser Pro Thr Glu Phe Gln Ala Ile Lys Ala Asn
    290                 295                 300

Ile Lys Ser Asn Ile Gln Gly Lys Cys Thr Ile Thr Pro Phe Leu His
```

```
                305                 310                 315                 320
Val Cys Trp Phe Val Ser Leu His Arg Trp Gly Lys Phe Phe Lys Pro
                    325                 330                 335

Leu Asn Phe Glu Trp Leu Thr Asp Ile Phe Ile Pro Ala Asp Cys Arg
                340                 345                 350

Ser Gln Leu Pro Asp Asp Asp Glu Met Arg Gln Met Tyr Arg Tyr Gly
                355                 360                 365

Ala Asn Val Gly Phe Ile Asp Phe Thr Pro Trp Ile Ser Glu Phe Asp
                370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                    405                 410                 415

Gly Phe Asn Ile Gln Gly Phe Val Gln Lys Tyr Val Asn Ile Asp Lys
                420                 425                 430

Val Met Cys Asp Arg Ala Ile Gly Lys Arg Gly Gly Thr Leu Leu
                435                 440                 445

Ser Asn Val Gly Leu Phe Asn Gln Leu Glu Glu Pro Asp Ala Lys Tyr
450                 455                 460

Ser Ile Cys Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                    485                 490                 495

Val Val Ala Ser Thr Lys Asn Val Val Gly Ser Gln Glu Ser Leu Glu
                500                 505                 510

Glu Leu Cys Ser Ile Tyr Lys Ala Leu Leu Leu Gly Pro
                515                 520                 525

<210> SEQ ID NO 6
<211> LENGTH: 525
<212> TYPE: PRT
<213> ORGANISM: Saccharomyces bayanus

<400> SEQUENCE: 6

Met Asn Thr Tyr Ser Glu Lys Thr Ser Leu Val Gln Asp Glu Cys Leu
1               5                   10                  15

Ala Lys Met Ile Gln Asn Gly His Ser Arg Arg Met Gly Ser Val Glu
                20                  25                  30

Asp Leu Tyr Ala Ala Leu Asn Arg Gln Lys Leu Tyr Arg Asn Phe Ser
                35                  40                  45

Thr Tyr Ser Glu Leu Asn Asp Tyr Cys Thr Lys Asp Gln Leu Ala Leu
            50                  55                  60

Ala Leu Arg Asn Ile Cys Leu Lys Asn Pro Thr Leu Leu His Ile Val
65                  70                  75                  80

Leu Pro Ala Arg Trp Pro Asp His Glu Asn Tyr Tyr Leu Ser Ser Glu
                85                  90                  95

Tyr Tyr Ser Gln Pro His Pro Lys His Asp Tyr Ile Ser Val Leu Pro
                100                 105                 110

Glu Leu Lys Phe Asp Gly Val Ile Leu Asn Glu Gln Pro Glu His Asn
            115                 120                 125

Ala Leu Met Lys Gln Ile Leu Glu Glu Leu Lys Asp Ser Asn Gly Ser
        130                 135                 140

Tyr Thr Ala Lys Ile Phe Lys Leu Thr Thr Ala Leu Thr Ile Pro Tyr
145                 150                 155                 160
```

Ala Gly Pro Thr Ser Pro Thr Trp Arg Leu Ile Cys Leu Pro Glu Glu
            165                 170                 175

Gly Tyr Thr Asp Lys Trp Lys Lys Phe Ile Phe Leu Ser Asn His Cys
            180                 185                 190

Met Cys Asp Gly Arg Thr Ser Ile His Phe Phe Gln Asp Leu Arg Asp
            195                 200                 205

Glu Leu Asn Asn Ile Lys Thr Pro Pro Lys Lys Leu Asp Tyr Ile Phe
            210                 215                 220

Gln Tyr Glu Lys Asp Tyr Gln Leu Leu Arg Lys Leu Pro Glu Pro Ile
225                 230                 235                 240

Glu Asn Met Ile Asp Phe Arg Pro Pro Tyr Met Phe Ile Pro Lys Ser
            245                 250                 255

Leu Ile Ser Gly Phe Ile Tyr Ser His Leu Arg Phe Ser Ser Lys Gly
            260                 265                 270

Val Cys Thr Arg Met Asp Glu Leu Glu Lys Asn Asp Asp Ile Val Thr
            275                 280                 285

Glu Ile Ile Thr Ile Ser Pro Ser Glu Leu Gln Lys Ile Arg Thr Lys
            290                 295                 300

Ile Lys Ser Asn Ile Pro Gly Lys Cys Thr Ile Thr Pro Phe Leu Glu
305                 310                 315                 320

Val Cys Trp Phe Val Ser Leu His Lys Trp Gly Lys Phe Phe Lys Pro
            325                 330                 335

Leu Lys Phe Glu Trp Leu Thr Asp Val Phe Ile Pro Ala Asp Cys Arg
            340                 345                 350

Ser Leu Leu Pro Glu Asp Glu Asp Val Arg Ala Met Tyr Arg Tyr Gly
            355                 360                 365

Ala Asn Val Gly Phe Val Asp Phe Thr Pro Trp Ile Ser Glu Phe Asn
            370                 375                 380

Met Asn Asp Ser Lys Glu Asn Phe Trp Pro Leu Ile Ala His Tyr His
385                 390                 395                 400

Glu Val Ile Ser Gly Ala Ile Asn Asp Lys His Leu Asn Gly Leu
            405                 410                 415

Gly Phe Asn Ile Gln Gly Leu Val Gln Lys Tyr Val Asn Ile Asp Lys
            420                 425                 430

Val Met Arg Asp Arg Ala Leu Gly Lys Ser Arg Gly Gly Thr Leu Leu
            435                 440                 445

Ser Asn Val Gly Ile Phe His Gln Ser Glu Glu Thr Asp Ser Arg Tyr
            450                 455                 460

Ser Ile Arg Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
            485                 490                 495

Val Ile Ser Ser Thr Lys Asn Ala Val Gly Ser Gln Glu Leu Leu Glu
            500                 505                 510

Glu Leu Cys Ala Met Tyr Lys Ala Leu Leu Leu Asp Pro
            515                 520                 525

<210> SEQ ID NO 7
<211> LENGTH: 524
<212> TYPE: PRT
<213> ORGANISM: Saccharomyces mikatae

<400> SEQUENCE: 7

Met Asn Glu Leu Thr Glu Lys His Ile Pro Val Gln His Glu Cys Leu
1               5                   10                  15

```
Glu Lys Met Ile Gln Asn Gly His Ala Arg Arg Met Gly Ser Val Glu
             20                  25                  30
Asp Leu Tyr Val Ala Leu Asn Arg Gln Asn Leu Tyr Arg Asn Phe Ser
             35                  40                  45
Thr Tyr Ala Glu Leu Thr Asp Tyr Cys Thr Arg Asp Gln Leu Thr Leu
 50                  55                  60
Ala Leu Arg Glu Leu Cys Leu Lys Asn Pro Thr Leu Leu His Ile Val
65                   70                  75                  80
Leu Pro Thr Arg Trp Pro Asn His Glu Thr Tyr Tyr Arg Ser Ser Glu
                 85                  90                  95
Tyr Tyr Ser Arg Pro His Pro Lys His Asp Tyr Ile Ser Val Leu Gln
             100                 105                 110
Glu Leu Lys Leu Asp Gly Val Val Leu Asn Asp Gln Pro Gln Tyr Ser
             115                 120                 125
Ala Ile Met Lys Gln Ile Leu Glu Glu Phe Lys Asn Ser Asn Gly Thr
130                 135                 140
Tyr Thr Ala Lys Ile Phe Lys Tyr Thr Thr Lys Leu Thr Ile Pro Tyr
145                 150                 155                 160
Phe Gly Pro Asn Gly Pro Asn Trp Arg Leu Ile Cys Leu Pro Glu Glu
                 165                 170                 175
His Thr Asp Arg Trp Lys Lys Phe Ile Phe Val Ser Asn His Cys Met
             180                 185                 190
Ser Asp Gly Arg Ser Ser Ile His Phe Phe His Asp Leu Arg Asp Glu
             195                 200                 205
Leu Asn Arg Ile Lys Thr Pro Pro Arg Lys Thr Asp Tyr Ile Phe Gln
             210                 215                 220
Tyr Glu Ser Asp Tyr Gln Leu Leu Arg Lys Leu Pro Glu Pro Ile Glu
225                 230                 235                 240
Arg Val Ile Asp Phe Arg Pro Pro Tyr Leu Phe Ile Pro Lys Ser Leu
                 245                 250                 255
Phe Ser Gly Phe Ile Tyr Asn His Leu Arg Phe Ser Ser Lys Gly Ile
             260                 265                 270
Cys Met Arg Met Glu Asp Met Glu Lys Cys Asp Asp Val Val Thr Asp
             275                 280                 285
Ile Ile Thr Ile Thr Pro Ser Glu Leu Gln Glu Ile Arg Ala Lys Ile
             290                 295                 300
Lys Leu Asn Ile Gln Gly Lys Cys Thr Ile Thr Pro Phe Leu Gln Val
305                 310                 315                 320
Cys Trp Phe Val Ser Leu His Lys Trp Gly Lys Phe Phe Lys Pro Leu
                 325                 330                 335
Asn Phe Glu Trp Leu Thr Asp Ile Phe Ile Pro Ala Asp Cys Arg Ser
             340                 345                 350
Glu Leu Pro Asp Asp Glu Glu Val Arg Gln Met Tyr Arg Tyr Gly Ala
             355                 360                 365
Asn Val Gly Phe Val Asp Phe Thr Pro Trp Ile Ser Glu Phe Asp Met
             370                 375                 380
Asn Asp Ser Glu Glu Asn Phe Trp Pro Leu Ile Lys His Tyr His Glu
385                 390                 395                 400
Val Ile Ser Ala Ala Leu Lys Asp Lys Lys His Leu His Gly Leu Gly
                 405                 410                 415
Phe Asn Ile Gln Gly Phe Val Gln Lys Tyr Val Asn Ile Asp Lys Ala
             420                 425                 430
```

```
Met Cys Asp Arg Ala Ile Gly Lys Ala Arg Gly Gly Thr Leu Leu Ser
            435                 440                 445

Asn Val Gly Met Phe Asn Gln Val Lys Glu Pro Asp Thr Lys Tyr Ser
        450                 455                 460

Ile Arg Asp Leu Ala Phe Gly Gln Phe Gln Gly Ser Trp His Gln Ala
465                 470                 475                 480

Phe Ser Leu Gly Val Cys Ser Thr Asn Val Lys Gly Met Asn Ile Leu
                485                 490                 495

Val Ala Ser Thr Lys Asn Val Val Gly Ser Gln Glu Ser Leu Glu Glu
            500                 505                 510

Leu Cys Ser Ile Phe Lys Ser Leu Leu Leu Gly Thr
            515                 520

<210> SEQ ID NO 8
<211> LENGTH: 524
<212> TYPE: PRT
<213> ORGANISM: Saccharomyces kudriavzevii

<400> SEQUENCE: 8

Met Thr Lys Ile Ser Glu Glu His Phe Pro Ile Gln His Glu Cys Leu
1               5                   10                  15

Glu Arg Met Ile Gln Asn Gly His Ala Arg Arg Met Gly Ser Val Glu
            20                  25                  30

Asp Leu Tyr Val Ala Leu Asn Arg Gln Lys Leu Tyr Arg Asn Phe Ser
        35                  40                  45

Ala Tyr Ala Glu Leu Ser Asp Tyr Cys Ser Lys Asp Gln Leu Thr Leu
    50                  55                  60

Ala Leu Arg Asn Ile Cys Leu Lys Asn Pro Thr Leu Leu His Ile Val
65                  70                  75                  80

Leu Pro Thr Arg Trp Pro Asp His Glu Asn Tyr Tyr Leu Ser Ser Glu
                85                  90                  95

Tyr Tyr Ser His Pro His Pro Glu His Asp Tyr Ile Ser Val Leu Pro
            100                 105                 110

Glu Leu Lys Leu Asp Gly Val Ile Ile Asn Glu Gln Pro Glu Asn Gly
        115                 120                 125

Lys Ile Val Arg Gln Ile Leu Glu Glu Phe Arg Asn Ser Asn Gly Thr
    130                 135                 140

Tyr Asn Ala Lys Ile Phe Lys Leu Thr Thr Ala Leu Thr Ile Pro Tyr
145                 150                 155                 160

Phe Gly Pro Thr Ser Pro Asn Trp Arg Leu Ile Cys Leu Pro Glu Glu
                165                 170                 175

His Thr Asp Lys Trp Lys Lys Phe Ile Phe Val Ser Asn His Cys Met
            180                 185                 190

Ser Asp Gly Arg Ser Ser Ile His Phe His Asp Leu Lys Ala Glu
        195                 200                 205

Leu Asn Asp Ile Lys Thr Pro Pro Lys Lys Leu Asp Tyr Leu Phe Lys
    210                 215                 220

Tyr Glu Asn Asp Tyr Gln Leu Leu Arg Lys Leu Pro Glu Pro Ile Glu
225                 230                 235                 240

Lys Val Ile Asp Phe Arg Pro Tyr Leu Phe Ile Pro Lys Ser Leu
                245                 250                 255

Leu Ser Gly Phe Ile Tyr Asn His Leu Arg Phe Ala Ser Arg Gly Ile
            260                 265                 270

Cys Thr Arg Met Asp Asp Met Glu Lys Ser Asp Asp Val Val Ala Glu
        275                 280                 285
```

```
Ile Ile Thr Ile Ser Pro Ser Glu Leu Gln Glu Ile Arg Thr Lys Ile
    290                 295                 300

Lys Ser Asn Ile Gln Gly Lys Cys Thr Leu Thr Pro Phe Leu Gln Val
305                 310                 315                 320

Cys Trp Phe Val Ser Leu His Gln Trp Gly Lys Phe Phe Lys Pro Leu
                325                 330                 335

Asn Phe Glu Trp Leu Thr Asp Ile Phe Ile Pro Ala Asp Cys Arg Pro
                340                 345                 350

Gln Leu Pro Asp Asp Glu Glu Val Arg Gln Met Tyr Arg Tyr Gly Ala
            355                 360                 365

Asn Val Gly Phe Val Asp Phe Thr Pro Trp Ile Cys Glu Ser Asn Met
    370                 375                 380

Asn Asp Asn Lys Glu Asn Phe Trp Pro Leu Ile Glu His Tyr His Gln
385                 390                 395                 400

Val Ile Ser Gly Ala Leu Arg Asp Asn Lys His Leu His Gly Leu Gly
                405                 410                 415

Leu Asn Ile Gln Gly Phe Val Gln Lys Tyr Val Asn Ile Asp Lys Ala
                420                 425                 430

Met Cys Asp Arg Ala Ile Gly Lys Ala Arg Gly Gly Thr Leu Leu Ser
            435                 440                 445

Asn Val Gly Met Phe Lys Gln Leu Asp Ser Ser Asn Cys Asn Tyr Ser
    450                 455                 460

Ile Lys Asp Leu Ala Phe Gly Gln Phe Gln Gly Ser Trp His Gln Ala
465                 470                 475                 480

Phe Ser Leu Gly Val Cys Ser Thr Asp Val Lys Gly Met Asn Ile Ile
                485                 490                 495

Val Ala Ser Thr Lys Asn Val Val Gly Ser Gln Glu Ser Leu Glu Glu
            500                 505                 510

Leu Cys Arg Val Tyr Lys Ala Met Leu Leu Gly Pro
    515                 520

<210> SEQ ID NO 9
<211> LENGTH: 1578
<212> TYPE: DNA
<213> ORGANISM: Saccharomyces cerevisiae

<400> SEQUENCE: 9
atgaacgaga ttgatgagaa gaaccaggct cccgttcagc aggagtgtct gaaggagatg    60
attcagaacg ccacgctcg acgaatggga tctgttgagg atctctacgt tgctctcaac    120
cgacagaacc tttaccgaaa cttctgtact tacggtgagc tttctgatta ctgtacccga    180
gatcagctca ctctcgctct tcgagagatt tgtctgaaga accctaccct ccttcacatt    240
gttcttccca ctcgatggcc taaccacgag aactactacc gatcttccga gtactactct    300
cgacctcacc ccgttcacga ttacatttct gttctccagg agcttaagct gtccggtgtg    360
gttctcaacg agcagcctga gtactctgct gttatgaagc agattcttga ggagttcaag    420
aactctaagg gttcctacac tgctaagatt tttaagctca ccaccactct caccattccc    480
tacttcggtc ctaccggccc tcttggcga cttatttgtc tccctgagga gcacactgag    540
aagtggaaga agttcatctt gtttctaac cactgtatgt ctgatggtcg atcttccatc    600 cacttttttcc acgacctccg agacgagctt aacaacatta agactccccc taagaagctc    660
gattacattt tcaagtacga ggaggattac cagctcctttc gaaagctccc cgagcctattt    720 gagaaggtta ttgactttcg acctccctac cttttcattc ctaagtctct cctttctggt    780
```

```
ttcatctaca accaccttcg attttcttct aagggtgtct gtatgcgaat ggatgacgtt     840
gagaagaccg acgatgttgt caccgagatc atcaacattt ctcctaccga gtttcaggct     900
attaaggcta acattaagtc taacatccag ggtaagtgta ctattacccc ctttctccac     960
gtttgttggt ttgtttctct tcacaagtgg ggtaagtttt tcaagcctct caacttcgag    1020
tggcttaccg acatttttat ccccgctgat tgtcgatctc agcttcccga cgacgatgag    1080
atgcgacaga tgtaccgata cggagctaac gttggtttta ttgacttcac cccttggatt    1140
tctgagttcg atatgaacga caacaaggag aacttttggc ctctcattga gcactaccac    1200
gaggttattt ctgaggctct tcgaaacaag aagcaccttc acggcctcgg ttttaacatt    1260
cagggtttcg ttcagaagta cgttaacatt gataaggtta tgtgtgatcg agctattgga    1320
aagcgacgag gtggtactct cctttctaac gttggtcttt tcaaccagct tgaggagccc    1380
gatgccaagt actctatttg tgatctcgct tttggtcagt tccagggatc ttggcaccag    1440 gcttttttctc ttggtgtttg ttctactaac gttaagggaa tgaacattgt tgttgcttct    1500
actaagaacg ttgttggttc tcaggagtcc cttgaggagc tttgttctat ttacaaggct    1560
cttctcctcg gtccttaa                                                  1578

<210> SEQ ID NO 10
<211> LENGTH: 1578
<212> TYPE: DNA
<213> ORGANISM: Saccharomyces bayanus

<400> SEQUENCE: 10
atgaacacct actctgagaa gacctctctt gttcaggacg agtgtctggc taagatgatt       60
cagaacggtc actctcgacg aatgggctct gtcgaggacc tttacgccgc cctcaaccga      120
cagaagctct accgaaactt ctctacttac tctgagctga cgattactg cactaaggat       180 cagctcgctc ttgctctccg aaacatttgt ctgaagaacc ccactctcct tcacattgtt      240
cttcccgctc gatggcccga tcgcgagaac tactaccttt cttctgagta ctactctcag      300 ccccaccca agcacgatta catctctgtt cttcccgagc tgaagttcga tggtgtgatt       360
ctcaacgagc agcccgagca caacgccctt atgaagcaga ttcttgagga gcttaaggat      420
tccaacggtt cttacactgc taagatttc aagctcacta ccgctctcac tattccctac       480
gctggtccca cttctcccac ttggcgactg attttgtctgc ccgaggaggg atacaccgat     540
aagtggaaga agtttatttt ccttttccaac cactgcatgt gtgatggtcg aacctctatt      600
cacttctttc aggatctccg agatgagctt aacaacatca agactccccc caagaagctc     660
gactacattt tccagtacga gaaggactac cagcttctcc gaaagctccc cgagcccatt      720
gagaacatga ttgattttcg accccctac atgtttattc ccagtccct tatttccggc        780 ttcatttact cccaccttcg attctcctct aagggtgtgt gtacccgaat ggacgagctt      840
gagaagaacg acgatattgt tactgagatc atcaccatct ctccctctga gcttcagaag     900
attcgaacta agatcaagtc taacattccc ggcaagtgca ccatcactcc cttccttgag     960
gtttgttggt ttgtttctct ccacaagtgg ggcaagtttt tcaagcccct caagttcgag    1020
tggcttaccg atgttttat tcccgctgat tgccgatctc tgctcccga ggacgaggac      1080 gtgcgagcta tgtaccgata cggcgctaac gtcggttttg ttgacttcac tccctggatt    1140
tctgagttta acatgaacga ctctaaggag aacttctggc cccttattgc tcactaccac    1200
gaggttattt ctggtgccat caacgacaag aagcacctca acggtcttgg tttcaacatt    1260
```

```
cagggccttg tccagaagta cgtcaacatt gacaaggtga tgcgagatcg agcccttggt    1320
aagtcccgag gaggcaccct gctctctaac gtgggtattt ccaccagtc tgaggagact     1380 gactcccgat actctatccg agacctcgct ttcggtcagt ttcagggttc ttggcaccag    1440
gctttctctc tcggtgtttg ttccactaac gtgaagggaa tgaacattgt tatttcttcc   1500
actaagaacg ccgtgggttc ccaggagctc cttgaggagc tttgtgccat gtacaaggct   1560
ctgctccttg accccta                                                  1578
```

<210> SEQ ID NO 11
<211> LENGTH: 1575
<212> TYPE: DNA
<213> ORGANISM: Saccharomyces mikatae

<400> SEQUENCE: 11

```
atgaacgagc ttaccgagaa gcacattccc gttcagcacg agtgtctgga agagatgatt    60
cagaacggtc acgctcgacg aatgggctct gttgaggacc tttacgttgc cctcaaccga    120
cagaaccttt accgaaactt ctctacttac gccgagctta ccgattactg tacccgagat    180
cagcttaccc ttgctctccg agagctttgc ctcaagaacc ccaccctcct tcacattgtt    240
cttcccactc gatggcccaa ccacgagact tactaccgat cttctgagta ctactctcga    300
ccccacccca agcacgatta catttctgtt cttcaggagc ttaagctgga cggtgtggtt    360
ctcaacgatc agccccagta ctctgctatt atgaagcaga ttcttgagga gttcaagaac    420
tctaacggta cttacactgc taagattttc aagtacacta ccaagctgac cattccctac    480
ttcgacccca cgttcccaa ctggcgactt atctgtcttc ccgaggagca cactgaccga    540
tggaagaagt ttatctttgt ttctaaccac tgcatgtctg atggtcgatc ttctattcac    600
tttttccacg accttcgaga tgagcttaac cgaatcaaga ctccccccccg aaagactgac    660 tacattttcc agtacgagtc tgactaccag cttctccgaa agctccccga gcccatcgag    720
cgagtgattg actttcgacc ccctacctc tttattccca gtcccttttt ctctggattc    780
atctacaacc accttcgatt ttcttctaag ggtatttgta tgcgaatgga ggatatggag   840
aagtgtgatg acgttgttac cgacattatc actattactc cctctgagct tcaggagatt    900
cgagctaaga ttaagctcaa cattcagggc aagtgtacca tcactcccttccttcaggtt    960 tgttggtttg tttctcttca caagtggggc aagttttttca agcccctgaa ctttgagtgg    1020
ctcactgaca ttttttattcc cgctgattgc cgatctgagc ttcccgacga tgaggaggtg    1080
cgacagatgt accgatacgg cgctaacgtt ggttttgttg acttcacccc ctggatttct    1140
gagttcgata tgaacgactc tgaggagaac ttttggcccc ttattaagca ctaccacgag    1200
gttatttctg ccgcccttaa ggataagaag ccttcacg gactcggttt taacattcag    1260
ggcttcgtcc agaagtacgt gaacattgac aaggctatgt gtgatcgagc cattggaaag    1320
gcccgaggag gcacccttct ctctaacgtt ggtatgttca accaggtgaa ggagcccgac    1380
accaagtact ctattcgaga ccttgctttt ggtcagtttc agggatcttg gcaccaggct    1440
ttttctcttg gcgtttgttc cactaacgtg aagggaatga acattcttgt tgcttctacc    1500
aagaacgttg tgggctctca ggagtccctt gaggagcttt gctccatttt caagtccctg   1560
cttctcggaa cctaa                                                     1575
```

<210> SEQ ID NO 12
<211> LENGTH: 1575
<212> TYPE: DNA
<213> ORGANISM: Saccharomyces kudriavzevii

<400> SEQUENCE: 12

```
atgactaaga tttctgagga gcactttccc attcagcacg agtgtctgga gcgaatgatt    60
cagaacggac acgctcgacg aatgggctct gttgaggacc tttacgtggc cctcaaccga   120
cagaagctct accgaaactt ctctgcttac gccgagcttt ctgattactg ttctaaggat   180
cagctcactc tcgctctgcg aaacatctgc ctcaagaacc ccactctcct tcacattgtt   240
cttcccaccc gatggcccga ccacgagaac tactacctct cctctgagta ctactctcac   300
ccccaccccg agcacgatta catctctgtt ctccccgagc tgaagctcga tggtgttatt   360
atcaacgagc agcccgagaa cggtaagatt gtgcgacaga ttcttgagga gttccgaaac   420
tctaacggta cttacaacgc taagattttt aagctcacta ccgctcttac cattccctac   480
tttggtccca cttctcccaa ctggcgactt atctgcctcc ccgaggagca caccgataag   540
tggaagaagt ttatcttcgt ttctaaccac tgcatgtccg atggtcgatc ttctattcac   600
ttctttcacg acctgaaggc cgagcttaac gatattaaga ccccccccaa gaagctcgac   660
tacctttcca gtacgagaaa cgattaccag ctccttcgaa agctccccga gcccattgag   720
aaggtgattg atttccgacc ccctacctc tttattccca gtccctgct ctctggattc    780
atttacaacc accttcgatt tgcttcccga ggtatttgca ctcgaatgga cgatatggag   840
aagtctgacg atgttgttgc tgagatcatt actatttctc cctctgagct tcaggagatt   900
cgaactaaga tcaagtccaa cattcagggc aagtgtactc tcactcccttt tctccaggtt  960
tgttggtttg tctcccttca ccagtggggc aagttttca agcccctaaa ctttgagtgg   1020
cttaccgaca tcttcattcc cgctgattgc cgaccccagc ttcccgacga tgaggaggtg   1080
cgacagatgt accgatacgg cgctaacgtg ggttttgttg atttcactcc ctggatttgc   1140
gagtctaaca tgaacgacaa caaggagaac ttttggcccc ttatcgagca ctaccaccag   1200
gttatttctg gagcccttcg agataacaag caccttcacg gcctcggact caacattcag   1260
ggctttgtcc agaagtacgt caacattgat aaggctatgt gcgaccgagc tatcggaaag   1320
gcccgaggtg gtactctcct ttctaacgtt ggaatgttca agcagcttga ctcctccaac   1380
tgcaactact ctattaagga ccttgctttc ggacagtttc agggttcttg caccaggct    1440
tttctctcg tgtttgttc taccgatgtt aagggaatga acattattgt tgcttctact    1500
aagaacgttg ttggttctca ggagtcccctt gaggagcttt gccgagttta caaggctatg   1560
ctccttggcc cctaa                                                    1575
```

<210> SEQ ID NO 13
<211> LENGTH: 1575
<212> TYPE: DNA
<213> ORGANISM: Saccharomyces arboricolus

<400> SEQUENCE: 13

```
atggataaaa tcagtgaaaa gcatacacct atccaacacg aatgtctgga aaagatgatc    60
cagaacgggc atgctcggcg catgggatct gttgaagatt tgtacgctgc cctcaacaga   120
caaaaactat atcgcaactt ttcagcattt ggagagctca atgattattg taccaaagaa   180
cagcttacac tagctctgag aaatatatgt ttgaaaaatc caactctttt acatattgta   240
ttgccaacaa gatggccaga tcatgaaaat tattatctta gctcggaata ctattcacaa   300
ccccgcccca acatgattac cgtctcggtt ttacaagagt tgaagctaga tggtgtggtt   360
cttaatgaac agcctgagta cagtgcaatc atgaaacaaa ttttgacaga gttcaagaac   420
```

```
agcaatggtt cttatactgc aaaaatcttt aaactgacta cagctttgac cattccttat    480
tttggaccat cgggtccaac ttggagacta atttgtctcc cagaagaata cccagataag    540
tggaagaaat ttatattcgt atccaatcac tgtatgtctg atggtagaac ttcaattcat    600
ttttttcatg atctaagaga tgagctaaat aatatcaaaa ccgaaccggg aaaaacggac    660
tacattttcc agtacgaaag ggattatcaa cttttgagaa agctcccaga gccaatcgaa    720
aacgtaatag acttgagacc accatatctg tttattccaa agtctcttct ttcgggcttt    780
atttataatc gcttaagttt tgcttctaag gccatatgca cgagaatgga tgaaatggaa    840
aaaagtgatg aagttgttac cgagattatc actatttcac catcagagct acaagcgatt    900
aggacaaaaa ttaaagcaaa cattcaaggc aagtgcacta tcacgccatt tctacatgtt    960
tgttggtttg tagccgttca taatgggggc aaatatttca agccgtcgaa cttcgagtgg    1020
tttactgaca ttttttattcc ggcagatttc cgttcactac tacctgaaga tgaagaagtg    1080
agacagatgt atagatacgg tgctaacgtt ggatttgttg atttcacttc gtggataagc    1140
gagtttaata tgaatgacag caaagaaaaa ttctggccac ttattgcaca ttataatgaa    1200
atgatttctg aagccataag agataagaag cagaccaatg gtttagggtt gaatatacag    1260
ggctttgttc aaaatatat caatattgat aaagcaatgt gtgatcgagc cattgggaaa    1320
gcacgtggag gtacattgtt gagtaacgta ggtatgttta accagtctga ggagatcggt    1380
cgcagatatt ccataagaga tttggctttt ggtcagtttc aagggtcatg gcgccaagca    1440
ttctcattgg gtgtttgttc gactaatgtg aaagggatga atattcttat tgcttcaaca    1500
aaaaacgtcg ttgaagccaa agaattgttg gaagaacttt gctccattta caaggctctg    1560
cttttaagtc cttag                                                    1575
```

<210> SEQ ID NO 14
<211> LENGTH: 524
<212> TYPE: PRT
<213> ORGANISM: Saccharomyces arboricolus

<400> SEQUENCE: 14

```
Met Asp Lys Ile Ser Glu Lys His Thr Pro Ile Gln His Glu Cys Leu
1               5                   10                  15

Glu Lys Met Ile Gln Asn Gly His Ala Arg Arg Met Gly Ser Val Glu
            20                  25                  30

Asp Leu Tyr Ala Ala Leu Asn Arg Gln Lys Leu Tyr Arg Asn Phe Ser
        35                  40                  45

Ala Phe Gly Glu Leu Asn Asp Tyr Cys Thr Lys Glu Gln Leu Thr Leu
    50                  55                  60

Ala Leu Arg Asn Ile Cys Leu Lys Asn Pro Thr Leu Leu His Ile Val
65                  70                  75                  80

Leu Pro Thr Arg Trp Pro Asp His Glu Asn Tyr Tyr Leu Ser Ser Glu
                85                  90                  95

Tyr Tyr Ser Gln Pro Arg Pro Lys His Asp Tyr Val Ser Val Leu Gln
            100                 105                 110

Glu Leu Lys Leu Asp Gly Val Val Leu Asn Glu Gln Pro Glu Tyr Ser
        115                 120                 125

Ala Ile Met Lys Gln Ile Leu Thr Glu Phe Lys Asn Ser Asn Gly Ser
    130                 135                 140

Tyr Thr Ala Lys Ile Phe Lys Leu Thr Thr Ala Leu Thr Ile Pro Tyr
145                 150                 155                 160

Phe Gly Pro Ser Gly Pro Thr Trp Arg Leu Ile Cys Leu Pro Glu Glu
```

```
            165                 170                 175
Tyr Pro Asp Lys Trp Lys Phe Ile Phe Val Ser Asn His Cys Met
            180                 185                 190

Ser Asp Gly Arg Thr Ser Ile His Phe Phe His Asp Leu Arg Asp Glu
        195                 200                 205

Leu Asn Asn Ile Lys Thr Glu Pro Gly Lys Thr Asp Tyr Ile Phe Gln
    210                 215                 220

Tyr Glu Arg Asp Tyr Gln Leu Leu Arg Lys Leu Pro Glu Pro Ile Glu
225                 230                 235                 240

Asn Val Ile Asp Leu Arg Pro Pro Tyr Leu Phe Ile Pro Lys Ser Leu
                245                 250                 255

Leu Ser Gly Phe Ile Tyr Asn Arg Leu Ser Phe Ala Ser Lys Ala Ile
                260                 265                 270

Cys Thr Arg Met Asp Glu Met Glu Lys Ser Asp Glu Val Val Thr Glu
                275                 280                 285

Ile Ile Thr Ile Ser Pro Ser Glu Leu Gln Ala Ile Arg Thr Lys Ile
            290                 295                 300

Lys Ala Asn Ile Gln Gly Lys Cys Thr Ile Thr Pro Phe Leu His Val
305                 310                 315                 320

Cys Trp Phe Val Ala Val His Lys Trp Gly Lys Tyr Phe Lys Pro Ser
                325                 330                 335

Asn Phe Glu Trp Phe Thr Asp Ile Phe Ile Pro Ala Asp Phe Arg Ser
                340                 345                 350

Leu Leu Pro Glu Asp Glu Glu Val Arg Gln Met Tyr Arg Tyr Gly Ala
                355                 360                 365

Asn Val Gly Phe Val Asp Phe Thr Ser Trp Ile Ser Glu Phe Asn Met
    370                 375                 380

Asn Asp Ser Lys Glu Lys Phe Trp Pro Leu Ile Ala His Tyr Asn Glu
385                 390                 395                 400

Met Ile Ser Glu Ala Ile Arg Asp Lys Lys Gln Thr Asn Gly Leu Gly
                405                 410                 415

Leu Asn Ile Gln Gly Phe Val Gln Lys Tyr Ile Asn Ile Asp Lys Ala
                420                 425                 430

Met Cys Asp Arg Ala Ile Gly Lys Ala Arg Gly Thr Leu Leu Ser
            435                 440                 445

Asn Val Gly Met Phe Asn Gln Ser Glu Glu Ile Gly Arg Arg Tyr Ser
    450                 455                 460

Ile Arg Asp Leu Ala Phe Gly Gln Phe Gln Gly Ser Trp Arg Gln Ala
465                 470                 475                 480

Phe Ser Leu Gly Val Cys Ser Thr Asn Val Lys Gly Met Asn Ile Leu
                485                 490                 495

Ile Ala Ser Thr Lys Asn Val Val Gly Ser Gln Glu Leu Leu Glu Glu
            500                 505                 510

Leu Cys Ser Ile Tyr Lys Ala Leu Leu Leu Ser Pro
            515                 520

<210> SEQ ID NO 15
<211> LENGTH: 1572
<212> TYPE: DNA
<213> ORGANISM: Saccharomyces arboricolus

<400> SEQUENCE: 15
atggataaga tttctgagaa gcacactccc atccagcacg agtgtctgga gaagatgatc      60
cagaacggcc acgctcgacg aatgggctct gttgaggatc tctacgctgc cctcaaccga     120
```

```
cagaagctct accgaaactt ctctgctttt ggtgagctga acgattactg taccaaggag    180
cagcttaccc ttgctctgcg aaacatttgc ctcaagaacc ctaccctcct tcacattgtt    240
ctccctaccc gatggcctga ccacgagaac tactacctct cctctgagta ctactctcag    300
ccccgaccca agcacgatta cgtttctgtt ctccaggagc ttaagctcga tggtgtggtt    360
cttaacgagc agcctgagta ctctgccatc atgaagcaga ttcttaccga gttcaagaac    420
tctaacggtt cttacactgc taagatcttt aagctcacta ccgctcttac cattccttac    480
ttcggaccct ccggccctac ctggcgactt atttgtctcc tgaggagta ccctgacaag    540 tggaagaagt ttattttcgt ttccaaccac tgtatgtctg atggtcgaac ttctattcac    600
tttttccacg atctccgaga tgagcttaac aacatcaaga ccgagcctgg caagaccgac    660
tacattttcc agtacgagcg agattaccag cttctccgaa agctccctga gcccatcgag    720
aacgttatcg acctccgacc ccttacctc tttattccta agtctctcct ttccggcttt    780
atttacaacc gactttcttt tgcttctaag gccatctgca cccgaatgga tgagatggag    840
aagtctgatg aggttgttac cgagattatc actatttctc cctccgagct tcaggctatt    900
cgaactaaga ttaaggccaa cattcagggc aagtgcacta tcacccttt ccttcacgtt    960 tgttggtttg tcgccgttca caagtggggc aagtacttca agccttccaa cttcgagtgg   1020
ttcactgaca ttttattcc cgctgatttc cgatcccttc tccctgagga tgaggaggtg   1080
cgacagatgt accgatacgg tgctaacgtt ggattcgttg atttcacttc ctggattcc   1140 gagtttaaca tgaacgactc taaggagaag ttctggcccc ttattgctca ctacaacgag   1200
atgatttctg aggctattcg agataagaag cagaccaacg tcttggcct caacattcag   1260 ggtttcgtgc agaagtacat caacattgat aaggctatgt gtgatcgagc cattggaaag   1320
gcccgaggtg gcactctcct gtccaacgtt ggcatgttca accagtctga ggagatcgga   1380
cgacgatact ccattcgaga cctcgctttt ggtcagtttc agggatcttg gcgacaggct   1440
ttctctctcg gtgtttgttc cactaacgtg aagggtatga acattcttat tgcttctacc   1500
aagaacgttg tgggctctca ggagcttctg gaggagcttt gctccattta caaggctctg   1560
ctcctttccc ct                                                       1572

<210> SEQ ID NO 16
<211> LENGTH: 1578
<212> TYPE: DNA
<213> ORGANISM: Saccharomyces bayanus

<400> SEQUENCE: 16
atgaatacct attcggaaaa aacctcgctg gtgcaagacg aatgtctggc caagatgatc     60
cagaatggcc attcgcggcg catgggctcg gtcgaagacc tgtacgccgc cctgaaccgc    120
cagaaactgt atcggaattt ctcgacctat tcggagctga tgattactg caccaaagat    180 caactggccc tggccctgcg caatatctgt ctgaaaaatc cgaccttct gcatatcgtg    240 ctgccggccc gctggccgga tcatgaaaat tattaccta gctcggaata ttattcgcag    300
ccgcatccga acatgattta tatctcggtg ctgccggagc tgaaattcga tggcgtgatc    360 ctgatgagc aaccggagca caatgccctg atgaagcaaa tccttgaaga actgaaggat    420
agcaatggct cgtataccgc gaaaatcttc aagctgacca ccgccctgac catcccgtac    480
gccggcccga cctcgccgac ctggcggctg atctgcctgc cggaagaagg ctacaccgat    540
aagtggaaga aattcatctt tctgtcgaat cactgcatgt gtgatggccg cacctcgatc    600
```

```
cacttttttcc aggatctgcg cgatgaactg aacaatatca aaaccccgcc gaagaaactg    660
gactacatct tccagtacga aaaggactac caactgctgc gcaagctgcc ggaaccgatc    720
gaaaatatga tcgattttcg cccgccctat atgtttatcc cgaagtcgct gatctcgggc    780
ttcatctact cgcatctgcg cttctcgtcg aagggcgtgt gcacgcgcat ggatgagctg    840
gaaaagaatg atgatatcgt gaccgaaatc atcaccatct cgccgtcgga actgcaaaag    900
atccgcacga aaatcaaatc gaacatcccg ggcaagtgca ccatcacccc gttcctggaa    960
gtgtgttggt ttgtgtcgct gcataagtgg ggcaagtttt caaaccgct gaagttcgag     1020 tggcttaccg atgtgtttat cccggccgat tgccgctcgc tgctgccgga agatgaagat    1080
gtgcgcgcca tgtaccgcta cggcgccaac gtcggctttg tggacttcac cccgtggatc    1140
agcgaattta acatgaatga cagcaaagaa aatttctggc cgcttatcgc ccattatcat    1200
gaagtgatct cgggcgcgat caatgacaag aagcatctga atggcctggg cttcaatatc    1260
caaggcctgg tccaaaagta tgtcaacatc gacaaagtga tgcgcgatcg cgcccttggc    1320
aaatcgcgcg gcggcacgct gctgtcgaac gtgggcatct ccatcaatc ggaggagacc     1380 gactcgcgct attcgatccg cgatctggcc ttcggccaat tccaaggctc gtggcatcaa    1440
gccttttcgc tgggcgtgtg ttcgaccaat gtgaagggca tgaacatcgt gatctcgtcg    1500
accaaaaatg ccgtgggcag ccaagaactg ctggaggaac tttgcgccat gtacaaggcc    1560
ctgctgctgg acccgtga                                                  1578

<210> SEQ ID NO 17
<211> LENGTH: 1578
<212> TYPE: DNA
<213> ORGANISM: Saccharomyces cerevisiae

<400> SEQUENCE: 17
atgaatgaaa tcgatgagaa gaatcaggcc cccgtgcagc aggaatgcct gaaagaaatg     60
atccagaatg ccatgcccg gcgcatgggc tcggtcgaag atctgtatgt ggcgctgaat    120
cgccaaaacc tgtatcgcaa cttctgcacc tatggcgaac tgtcggatta ttgcacgcgg    180
gatcagctga ccctggcgct gcgggaaatc tgcctgaaaa atccgacgct gctgcatatc    240
gtgctgccca cccggtggcc caatcatgaa aattattatc gctcgtcgga atactattcg    300
cggccccatc cggtgcatga ttatatcagc gtgctgcaag aactgaaact gagcggcgtg    360
gtcctgaatg aacaaccgga gtactcggcc gtgatgaagc aaatcctgga agaattcaaa    420
aattcgaagg gctcgtatac cgccaagatc ttcaagctga ccaccaccct gaccatcccg    480
tacttcggcc cgaccggccc cgtcgtggcg gctgatctgcc tgccggaaga gcacaccgaa    540
aagtggaaga agttcatctt cgtgtcgaat cattgcatgt cggatggccg gtcgtcgatc    600
cacttcttcc atgatctgcg cgacgaactg aataatatca aaaccccgcc gaagaaactg    660
gattacatct tcaagtacga ggaggattac caactgctgc gcaaactgcc ggaaccgatc    720
gaaaaggtga tcgactttcg cccgccgtac ctgtttatcc cgaagtcgct gctttcgggc    780
ttcatctaca atcatctgcg cttttcgtcg aaaggcgtct gcatgcgcat ggatgatgtg    840
gaaaaaaccg atgatgtggt caccgagatc atcaatatct cgccgaccga atttcaggcg    900
atcaaagcca atatcaaatc gaatatccaa ggcaagtgta ccatcacccc gtttctgcat    960
gtgtgttggt ttgtgtcgct tcataaatgg ggcaaattct caaaccgct gaacttcgaa     1020 tggcttacgg atatctttat cccgccgat tgccgctcgc aactgccgga tgatgatgaa     1080
atgcgccaga tgtaccgcta tggcgccaac gtgggctttta tcgacttcac ccctggatc    1140
```

```
agcgaatttg acatgaatga taacaaagaa aattttttggc cgcttatcga gcactaccat    1200
gaagtgatct cggaagccct gcgcaataaa aagcatctcc atggcctggg cttcaatatc    1260
caaggcttcg tgcaaaagta tgtgaacatc gacaaggtga tgtgcgatcg cgccatcggc    1320
aagcgccgcg gcggcaccct gctgagcaat gtgggcctgt taatcagct ggaggagccc    1380 gatgccaaat attcgatctg cgatctggcc tttggccaat ccaaggctc gtggcaccaa    1440 gccttttcgc tgggcgtgtg ttcgaccaat gtgaagggca tgaatatcgt ggtggcctcg    1500
accaagaatg tggtgggctc gcaagaatcg ctggaagagc tttgcagcat ctacaaagcc    1560
ctgcttctgg gcccgtga                                                  1578
```

<210> SEQ ID NO 18
<211> LENGTH: 1578
<212> TYPE: DNA
<213> ORGANISM: Saccharomyces cerevisiae

<400> SEQUENCE: 18

```
atgaatgaaa tcgatgagaa aaatcaggcc cccgtgcaac aagaatgcct gaaagagatg     60
attcagaatg ggcatgctcg gcgtatggga tctgttgaag atctgtatgt tgctctcaac    120
agacaaaact tatatcgaaa cttctgcact tatggagaat tgagtgatta ctgtactagg    180
gatcagctca cattagcttt gagggaaatc tgcctgaaaa atccaactct tttacatatt    240
gttctaccaa caagatggcc aaatcatgaa aattattatc gcagttccga atactattca    300
cggccacatc cagtgcatga ttatatttca gtattacaag aattgaaact gagtggtgtg    360
gttctcaatg aacaacctga gtacagtgca gtaatgaagc aaaatattag agaattcaaa    420
aatagtaagg gttcctatac tgcaaaaatt tttaaactta ctaccacttt gactattcct    480
tactttggac aacaggacc gagttggcgg ctaatttgtc ttccagaaga gcacacagaa    540
aagtggaaaa aatttatctt tgtatctaat cattgcatgt ctgatggtcg gtcttcgatc    600 cactttttc atgatttaag agacgaatta aataatatta aaactccacc aaaaaaatta    660
gattacattt tcaagtacga ggaggattac caattattga ggaaacttcc agaaccgatc    720
gaaaaggtga tagactttag accaccgtac ttgtttattc cgaagtcact tctttcgggt    780
ttcatctaca atcatttgag attttcttca aaaggtgtct gtatgagaat ggatgatgtg    840
gaaaaaaccg atgatgttgt caccgagatc atcaatattt caccaacaga atttcaagcg    900
attaaagcaa atattaaatc aaatatccaa ggtaagtgta ctatcactcc gttttttacat    960 gtttgttggt ttgtatctct tcataaatgg ggtaaatttt tcaaaccatt gaacttcgaa   1020
tggcttacgg atatttttat ccccgcagat tgccgctcac aactaccaga tgatgatgaa   1080
atgagacaga tgtacagata tggcgctaac gttggattta ttgacttcac ccctggata    1140 agcgaatttg acatgaatga taacaaagaa aattttttggc cacttattga gcactaccat   1200
gaagtaattt cggaagcatt aagaaataaa aagcatctcc atggcttagg gttcaatata   1260
caaggcttcg ttcaaaaata tgtgaacatt gacaaggtaa tgtgcgatcg tgccatcggg   1320
aaaagacgcg gaggtacatt gttaagcaat gtaggtctgt taatcagtt agaggagccc   1380 gatgccaaat attctatatg cgatttggca tttggccaat tcaaggatc ctggcaccaa   1440 gcattttcct tgggtgtttg ttcgactaat gtaaggggga tgaatattgt tgttgcttca   1500
acaaagaatg ttgttggtag tcaagaatct ctcgaagagc tttgctccat ttacaaagct   1560 ctcctttag gcccttag                                                  1578
```